US 11,369,179 B2

(12) United States Patent
Lau

(10) Patent No.: US 11,369,179 B2
(45) Date of Patent: Jun. 28, 2022

(54) CLAMPING HEAD FOR EPILATOR AND EPILATOR INCORPORATING SUCH

(71) Applicant: Heroka Industries Ltd., Kowloon (HK)

(72) Inventor: Shuwong Lau, Kowloon (HK)

(73) Assignee: HEROKA INDUSTRIES LTD., Kowloon (HK)

( * ) Notice: Subject to any disclaimer, the term of this patent is extended or adjusted under 35 U.S.C. 154(b) by 388 days.

(21) Appl. No.: 16/490,483

(22) PCT Filed: Feb. 26, 2018

(86) PCT No.: PCT/CN2018/077252
§ 371 (c)(1),
(2) Date: Aug. 30, 2019

(87) PCT Pub. No.: WO2018/157774
PCT Pub. Date: Sep. 7, 2018

(65) Prior Publication Data
US 2020/0015567 A1 Jan. 16, 2020

(30) Foreign Application Priority Data
Mar. 1, 2017 (HK) .................................. 17101598.5

(51) Int. Cl.
*A45D 26/00* (2006.01)
*A61B 17/00* (2006.01)
*B26B 19/38* (2006.01)

(52) U.S. Cl.
CPC ..... *A45D 26/0028* (2013.01); *A45D 26/0038* (2013.01); *A45D 2026/008* (2013.01);
(Continued)

(58) Field of Classification Search
CPC ............ A45D 26/0023; A45D 26/0028; A45D 26/0038; A45D 26/0042; A45D 2026/008;
(Continued)

(56) References Cited

U.S. PATENT DOCUMENTS

| 6,451,028 B1 | 9/2002 | Sanchez-Martinez et al. |
| 2008/0045975 A1 | 2/2008 | Sanchez-Martinez |

(Continued)

FOREIGN PATENT DOCUMENTS

| CN | 103298366 A | 9/2013 |
| CN | 105188462 A | 12/2015 |

(Continued)

OTHER PUBLICATIONS

Chinese Office Action for Application No. 201880015057.5, dated Jun. 3, 2020, 8 pages.
(Continued)

*Primary Examiner* — Robert A Lynch
(74) *Attorney, Agent, or Firm* — Morgan, Lewis & Bockius LLP

(57) ABSTRACT

Clamping heads are disclosed with epilators and clamping hairs, and can include a first clamping unit and at least two spring plates arranged adjacent to each other on a plane traversing an axis of rotation of a stopper plate, each of said spring plate having a first spring plate clamping surface, and said stopper plate is adjacent to said first clamping unit and having a stopper plate clamping surface opposing said first spring plate clamping surface of each said spring plate, such that during rotation of said stopper plate relative to said first clamping unit, said first clamping unit reciprocally moves away from and towards said stopper plate such that a first space between said first spring plate clamping surface and said stopper plate clamping surface opens and closes for clamping hair.

22 Claims, 24 Drawing Sheets

(52) U.S. Cl.
CPC ... *A61B 2017/00752* (2013.01); *B26B 19/382* (2013.01); *B26B 19/3813* (2013.01)

(58) Field of Classification Search
CPC ...... A61B 2017/00752; B26B 19/3813; B26B 19/382
See application file for complete search history.

(56) References Cited

U.S. PATENT DOCUMENTS

2009/0182349 A1\* 7/2009 Poran ................ A45D 26/0028
606/133
2014/0309663 A1  10/2014 Sanchez-Martinez et al.

FOREIGN PATENT DOCUMENTS

| JP | H06509960   | 11/1994 |
|----|-------------|---------|
| JP | 2002516125  | 6/2002  |
| JP | 2008514320 A| 5/2008  |

OTHER PUBLICATIONS

Japanese Office Action for Application No. 2019-557583, dated Mar. 10, 2020, 9 pages.
International Search Report and Written Opinion of the International Searching Authority, dated May 31, 2018, 9 pgs.

\* cited by examiner

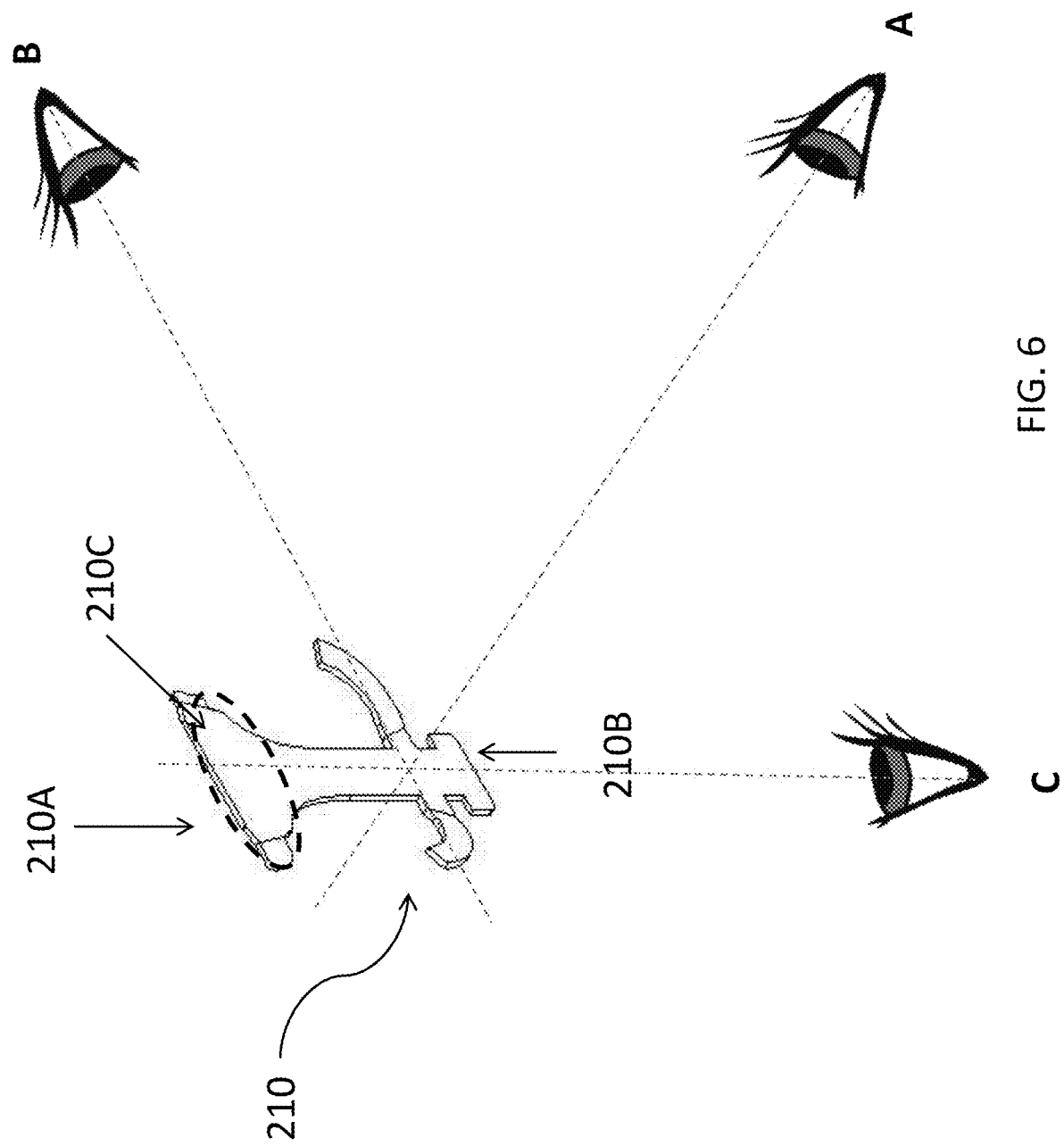

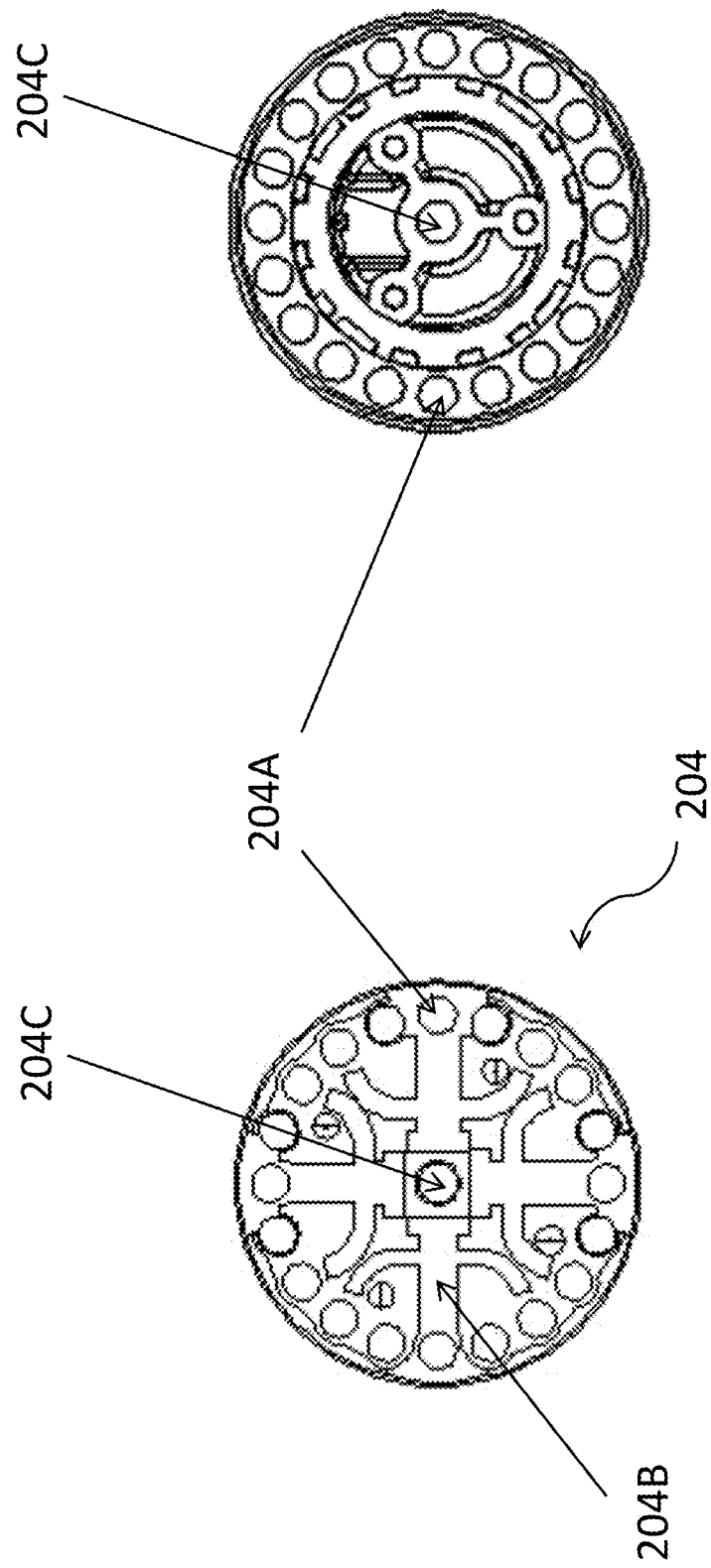

CLAMPING HEAD FOR EPILATOR AND EPILATOR INCORPORATING SUCH

FIELD OF THE INVENTION

This invention relates to a clamping head for clamping hairs, and in particular the clamping head attached to an epilator.

BACKGROUND

There are many types of epilators in the market to suit different needs of users. One particular type of these epilators disclosed in US2014309663 has a clamping head attached at one end of the epilator. The clamping head have an axle driven into motion by a motor about a center axle axis, and an end plate is arranged at a first end of the axle for rotation together with the axle. The end plate has at least a first functional surface and a first clamping element having a functional surface. The first functional surface of the end plate is arranged face-to-face with the functional surface of the first clamping element, and the first clamping element repeatedly moves towards and away from the end plate with a coil spring such that a closed position is obtained repeatedly when the two functional surfaces abut on each other. Any hair that may have been clamped in between the functional surfaces in the closed position will be plucked from skin. The assembly of the coil spring to the clamping element is complicated and difficult.

Therefore, the present invention seeks to address these problems, or at least to provide an alternative to the public. It is desirable to provide users an epilator having better clamping and durability. Meanwhile, from the perspective of manufacturing, it is also desirable to produce said epilator with less material with easier assembly.

SUMMARY

According to a first aspect of the present invention, there is provided a clamping head comprising:
  a first clamping unit may include at least two spring plates arranged adjacent to each other on a plane traversing an axis of rotation of a stopper plate, each said spring plate has a first spring plate end provides a first spring plate clamping surface;
  said stopper plate may be adjacent to said first clamping unit and having a stopper plate clamping surface opposing said first spring plate clamping surface of each said spring plate; during rotation of said stopper plate relative to said first clamping unit, said first clamping unit may reciprocally move away from and towards said stopper plate such that a first space between said first spring plate clamping surface and said stopper plate clamping surface opens and closes for clamping hair.

Preferably, said spring plate in said clamping head may be made of metal. More preferably, said stopper plate in said clamping head may be made of plastic.

Optionally, each said spring plate of said clamping head may have a second spring plate end opposing said first spring plate end which provides a second spring plate clamping surface. Preferably, said first clamping unit may only have two said spring plates. More preferably, said two spring plates may intersect orthogonally to each other. Advantageously, the clamping head may extend laterally along a handle of an epilator.

Optionally, each said spring plate of said clamping head may have a second spring plate end opposing said first spring plate end, said first spring plate end has a first pair of wings on said spring plate, and said second spring plate end has a second pair of wings on said spring plate, wherein said first pair of wings are biased to a first direction and said second pair of wings are biased to a second direction, wherein the first direction opposes the second direction. Preferably, said first clamping unit may have 4 said spring plates. Even more preferably, the clamping head may extend horizontally along a handle of an epilator.

Preferably, at least one of said spring plate of the clamping head may be biased to enable said first spring plate clamping surface thereof to engage with said stopper plate clamping surface to close said first space. Alternatively, at least one of said spring plate of the clamping head may be biased to enable said first spring plate clamping surface thereof to disengage with said stopper plate clamping surface to open said first space.

The clamping head may further comprise an actuating unit having:
  a plurality of actuators, each of said plurality of actuators has a first actuator end pointing towards said stopper plate clamping surface and a second actuator end opposing said first actuator end, each of said plurality of actuators being arranged along said axis of rotation;
  an end plate being arranged coaxially with said stopper plate, wherein said end plate has a plurality of actuator apertures corresponding to said plurality of actuators to allow respective said plurality of actuators extending through said end plate;
  a base member being arranged coaxially with said stopper plate, said base member has a base member surface on which has an actuating portion, said base member surface facing towards said stopper plate clamping surface.

Optionally, the actuating portion may be an axial protrusion protruded from said base member surface towards said stopper plate clamping surface. Preferably, said first actuator end may be adjacent to each end of each said spring plate of said first clamping unit, when said stopper plate rotates about said axis of rotation, said plurality of actuators also rotate about said axis of rotation, said second actuator end of each of said plurality of actuators take turn to push said axial protrusion to move towards said stopper plate clamping surface to close said first space.

Optionally, the actuating portion may be a recess on said base member surface. Preferably, said first actuator end may be adjacent to each end of each said spring plate of said first clamping unit, when said stopper plate rotates about said axis of rotation, said plurality of actuators also rotate about said axis of rotation, said second actuator end of each of said plurality of actuators take turn to enter into said recess to move away said stopper plate clamping surface to open said first space.

Preferably, said second actuator end may extend through said plurality of actuator apertures of said end plate. Alternatively, said first actuator end may extend through said plurality of actuator apertures of said end plate.

The clamping head may further comprise:
  a secondary clamping unit including at least two secondary spring plates arranged adjacent to each other on said plane traversing said axis of rotation of said stopper plate, each said secondary spring plate has a secondary first spring plate end provides a secondary first spring plate clamping surface;
  a middle plate being arranged coaxially with said stopper plate and adjacent to said secondary clamping unit, said middle plate have a first middle plate surface opposing said stopper plate clamping surface and a second middle plate surface opposing said secondary first spring plate clamping surface of each said secondary spring plate; during rotation of said middle plate relative to said secondary clamping unit, said secondary clamping unit reciprocally moves away from and towards said middle plate such that a second space between said secondary first spring plate clamping surface of said second clamping unit and said second middle plate surface opens and closes for clamping hair.

Preferably, said two secondary spring plates may intersect with each other orthogonally. More preferably, each said secondary spring plate may have a secondary second spring plate end opposing said secondary first spring plate end, said secondary first spring plate end has a first pair of wings on said secondary spring plate, and said secondary second spring plate end has a second pair of wings on said secondary spring plate, wherein said first pair of wings of said secondary spring plate are biased to a first direction from said secondary spring plate and said second pair of wings of said secondary spring plate are biased to a second direction from said secondary spring plate, wherein said first direction opposes said second direction.

According to a second aspect of the present invention, there is provided an epilator comprising a clamping head and an actuating unit, wherein: the clamping head may have a first clamping unit including at least two spring plates arranged adjacent to each other on a plane traversing an axis of rotation of a stopper plate, each said spring plate has a first spring plate end provides a first spring plate clamping surface, said stopper plate is adjacent to said first clamping unit and having a stopper plate clamping surface opposing said first spring plate clamping surface of each said spring plate, a first space is formed between said first spring plate clamping surface of each said spring plate and said stopper plate clamping surface for clamping hair; the actuating unit may have a plurality of actuators being arranged along said axis of rotation, each of said plurality of actuators has a first actuator end adjacent to each end of each said spring plate of said first clamping unit; when said stopper plate rotates about said axis of rotation, each of said plurality of actuators may reciprocally move away from and towards said stopper plate to open and close respective said first space.

BRIEF DESCRIPTION OF THE DRAWINGS

FIG. 6 shows a perspective view of spring plate 210 of the second embodiment of this invention;

FIGS. 12a and 12b show the views of end plate 204 viewed from angles A and B of FIG. 11, respectively;

DETAILED DESCRIPTION OF PREFERRED EMBODIMENTS OF THE INVENTION

Figure 1:
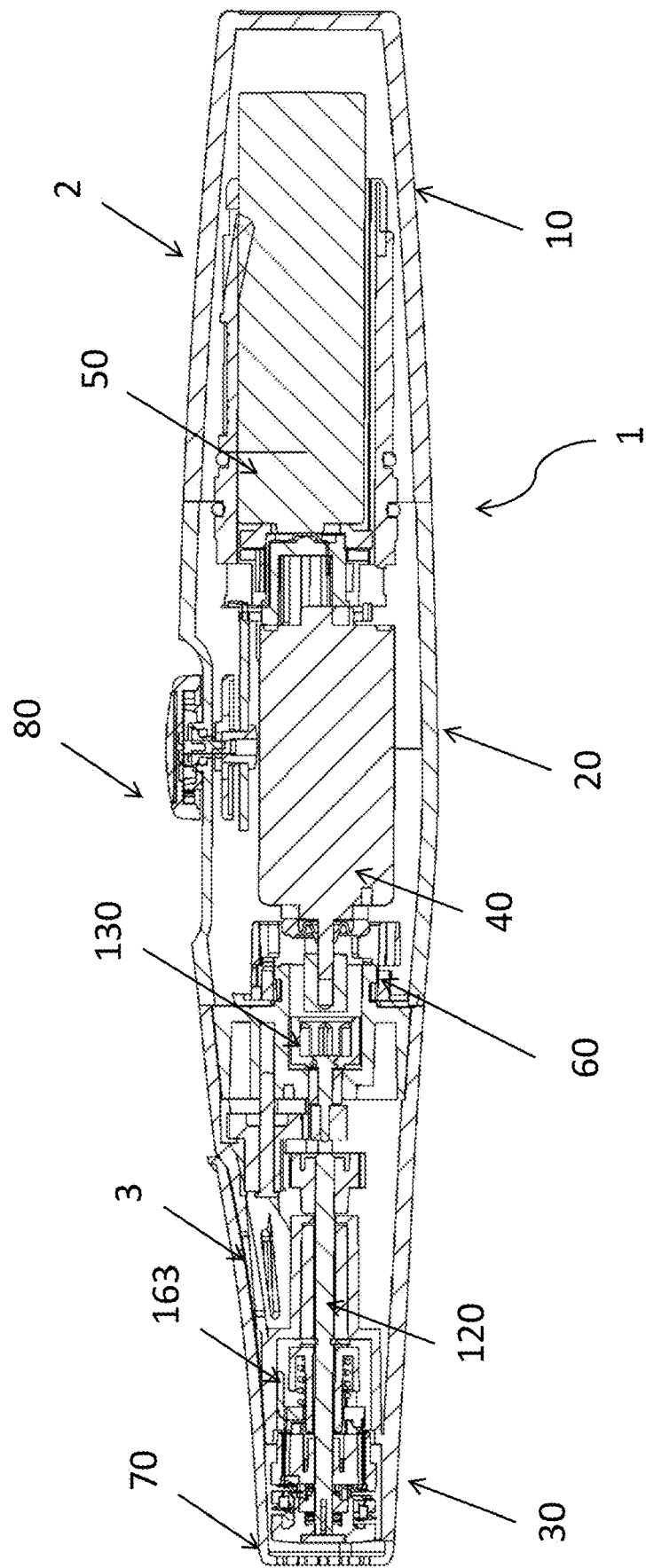
FIG. 1 shows a longitudinal cross-sectional of an epilator having a first embodiment of clamping head on an attachment of the present invention.
Figure 2:
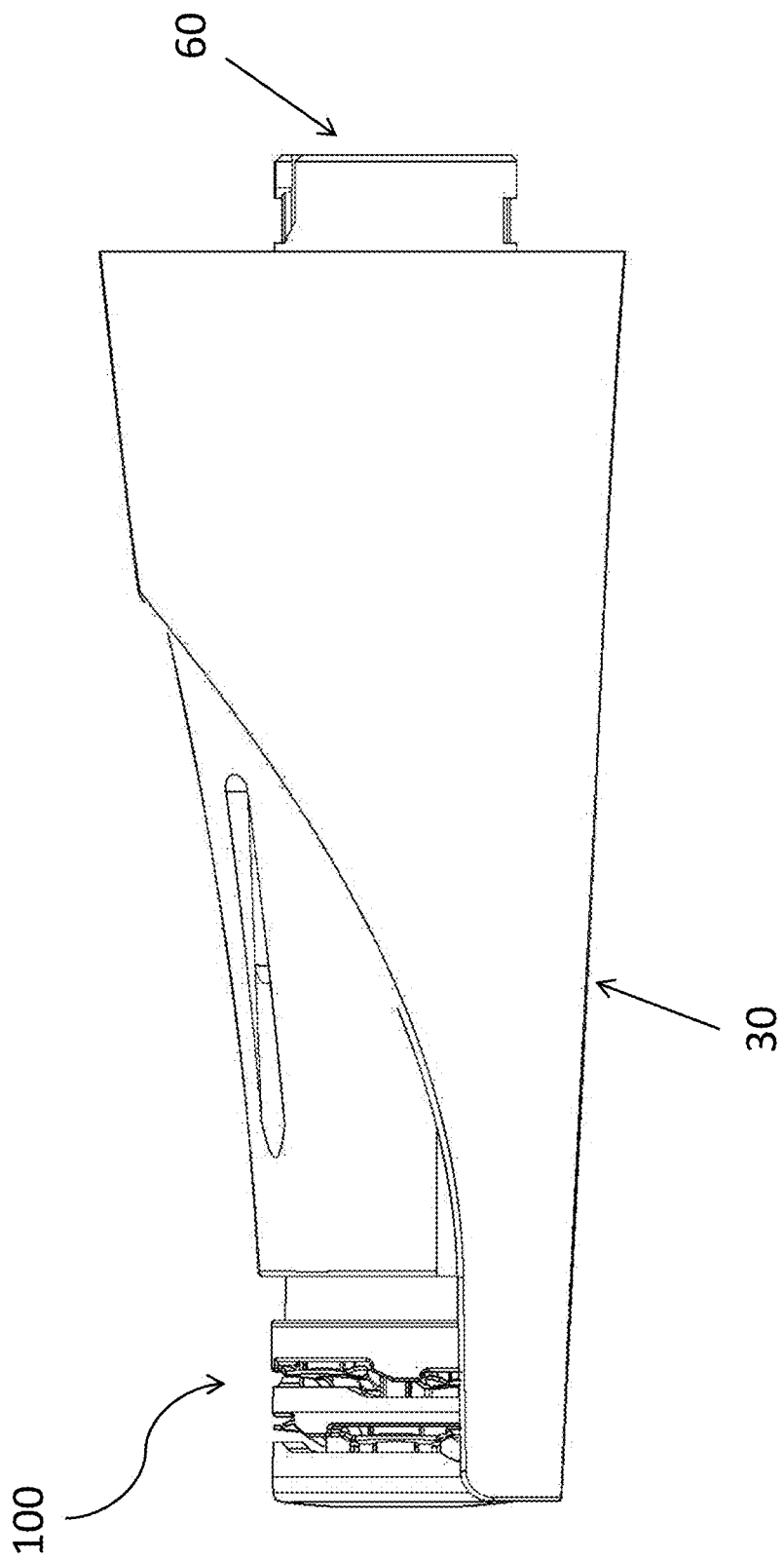
FIG. 2 shows a detached attachment from the epilator of FIG. 1.

This disclosure is now presented by way of examples with reference to the figures in the following paragraphs. Objects, features, and aspects of the present disclosure are disclosed in or are apparent from the following description. It is to be understood by one of ordinary skilled in the art that the following discussion is a description of exemplary embodiments only, and is not intended as limiting the broader aspects of the present disclosure, which broader aspects are embodied in the exemplary constructions. List 1 is a list showing the parts and respective reference numerals in the figures.

List 1

| Reference numeral | Part name |
| --- | --- |
| 1 | Epilator |
| 2 | Handle |
| 3 | Attachment |
| 10 | Battery housing |

-continued

| Reference numeral | Part name |
|---|---|
| 20 | Main housing |
| 30 | Attachment housing |
| 40 | Motor |
| 42 | Motor axle |
| 50 | Battery |
| 60 | Connector element |
| 70 | Protective cap |
| 80 | On/Off switch |
| 100 | Clamping head for the first embodiment of this invention |
| 110A | Shaft 1 |
| 110B | Connector |
| 110C | Bushing |
| 110D | Shaft 2 |
| 120 | Axle |
| 130A | Gear 1 |
| 130B | Gear 2 |
| 130C | Gear 3 |
| 141 | Stopper nut |
| 142 | Stopper plate |
| 142A | Stopper plate clamping surface |
| 151 | Spring plate |
| 151A | First spring plate clamping surface of spring plate 151 |
| 151B | Second spring plate clamping surface of spring plate 151 |
| 152 | Spring plate |
| 152A | First spring plate clamping surface of spring plate 152 |
| 152B | Second spring plate clamping surface of spring plate 152 |
| 160 | Middle plate |
| 160A | First middle plate surface |
| 160B | Second middle plate surface |
| 160C | Actuator apertures on middle plate160 |
| 161 | End plate |
| 161A | First end plate surface |
| 161B | Second endplate surface |
| 161C | Actuator aperture on end plate 161 |
| 162 | Base member |
| 162A | Base member surface |
| 162B | Base member actuating portion |
| 163 | Resilient member |
| 164 | Washer |
| 165 | E-ring |
| 166 | Spring holder |
| 167 | Main bushing |
| 171 | Spring plate |
| 171A | First spring plate clamping surface of spring plate171 |
| 171B | Second spring plate clamping surface of spring plate171 |
| 172 | Spring plate |
| 172A | First spring plate clamping surface of spring plate 172 |
| 172B | Second spring plate clamping surface of spring plate172 |
| 180 | Actuator |
| 180A | First actuator end of actuator 180 |
| 180B | Second actuator end of actuator 180 |
| 190 | Actuator |
| 190A | First actuator end of actuator 190 |
| 190B | Second actuator end of actuator 190 |
| 200 | Clamping head for the second embodiment of this invention |
| 201 | Axle |
| 202 | Base member |
| 202A | Base member actuating portion |
| 202B | Axle aperture on base member 202 |
| 202C | guiding track on base member 202 |
| 202D | First axial protrusion on base member 202 |
| 202E | Second axial protrusion on base member 202 |
| 203A | First gear |
| 203B | Second gear |
| 204 | End plate |
| 204A | Actuator aperture on end plate 204 |
| 204B | "Anchor" shaped recess on end plate 204 |
| 204C | Axle aperture on end plate 204 |
| 207 | Resilient member |
| 210 | Spring plate |
| 210A | First spring plate end |
| 210B | Second spring plate end |
| 210C | First Spring plate clamping surface of spring plate 210 |
| 210D | First pair of wings on spring plate 210 |

-continued

| Reference numeral | Part name |
|---|---|
| 210E | Second pair of wings on spring plate 210 |
| 220 | Stopper plate |
| 220A | Stopper plate clamping surface |
| 220B | Actuator aperture on stopper plate 220 |
| 220C | "Anchor" shaped recess on stopper plate 220 |
| 220D | Axle aperture on stopper plate 220 |
| 220E | Protrusions |
| 230 | Middle plate |
| 230A | Middle plate clamping surface |
| 230B | Actuator aperture on middle plate 230 |
| 230C | "Anchor" shaped recess on middle plate 230 |
| 230D | Axle aperture on middle plate 230 |
| 230E | Protrusions |
| 240 | Actuator |
| 240A | First actuator end of actuator 240 |
| 240B | Second actuator end of actuator 240 |
| 250 | Cover plate |
| 300 | Clamping head for the third embodiment of this invention |

An example of epilator 1 having clamping head 100 at a lateral side on attachment 3 is shown in FIG. 1. Epilator 1 has attachment 3 connected to handle 2 with connector element 60. Handle 2 is a hollow housing including battery housing 10 and main housing 20 to accommodate battery 50 and motor 40, respectively. Battery 50 powers motor 40 to rotate clamping head 100 about axle 120. Handle 2 further comprises on/off switch 80 on the peripheral of handle 2 for switching on/off of epilator 1 or the rotational speed of clamping head 100 or rotational direction of clamping head 100. Attachment 3 has attachment housing 30 and protective cap 70 covering clamping head 100. It is advantageously for attachment 3 to be detachable from handle 2 such that users can regularly clean attachment 3/clamping head 100 or even change another attachment 3 due to hygienic reasons, or to replace attachment 3 when necessary.

Figure 3:
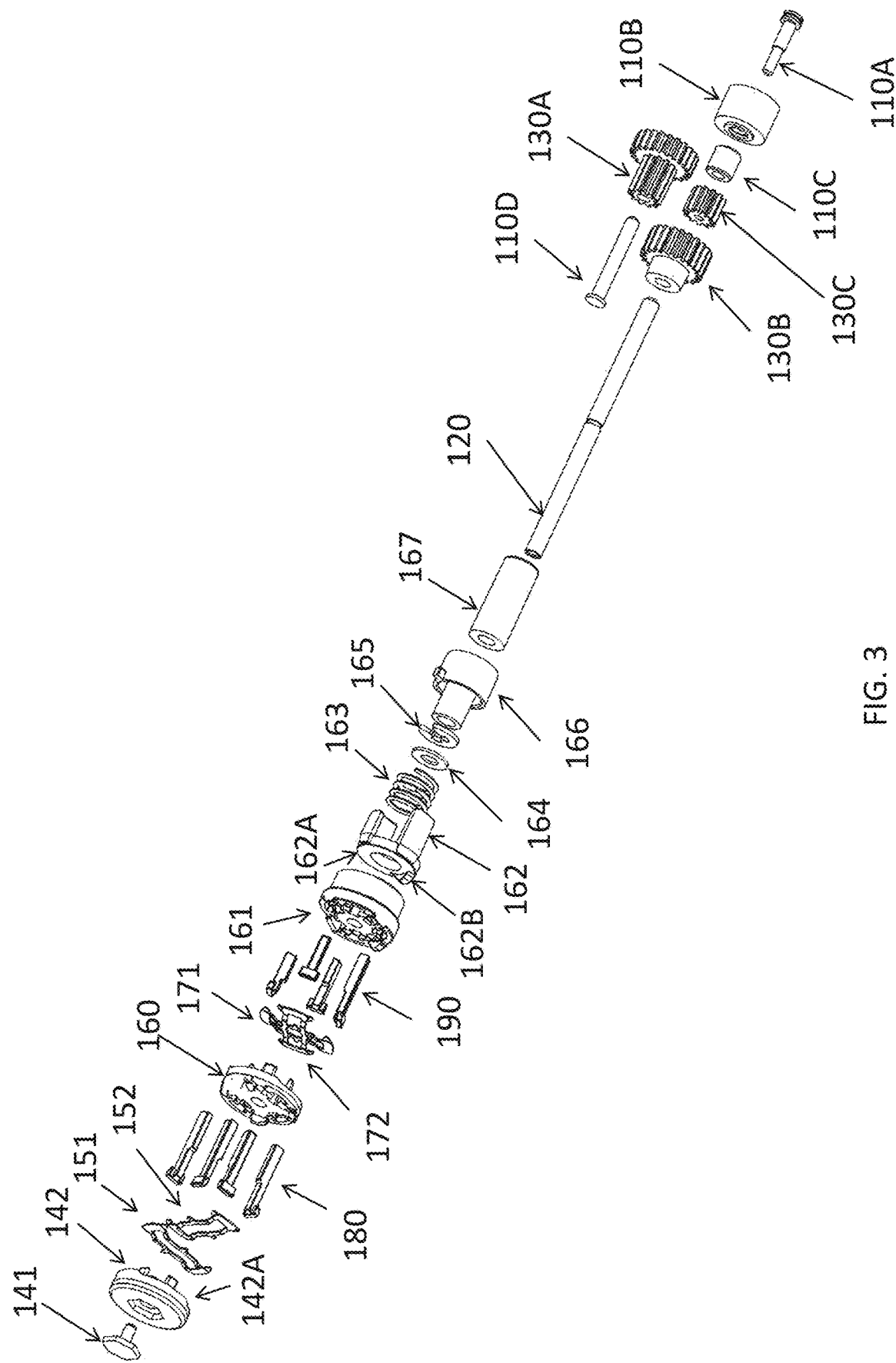
FIG. 3 shows an exploded view of the clamping head of FIG. 1.

As shown in FIGS. 1 and 3, epilator 1 comprises a gear unit having gears 130A, 130B, and 130C; shafts 110A and 110D; connector 110B; bushing 110C for coupling motor axle 42 of motor 40 with axle 120 such that axle 120 is driven into motion by motor 40. FIGS. 1 and 3 show that shaft 110A is an extension to the motor axle of motor 40, thus axle 120 is an extension of shaft 110A when axle 120 is coupled to shaft 110A by means of the gear unit. However, it could be understood that in some embodiments, epilator 1 can have attachment 3 which may be inclined with respective to the center axis of handle 2 so as to provide comfort for users to use the epilator. Further, rotation of axle 120 by motor 40 could be achieved by various different manners known in the art.

Figure 4:
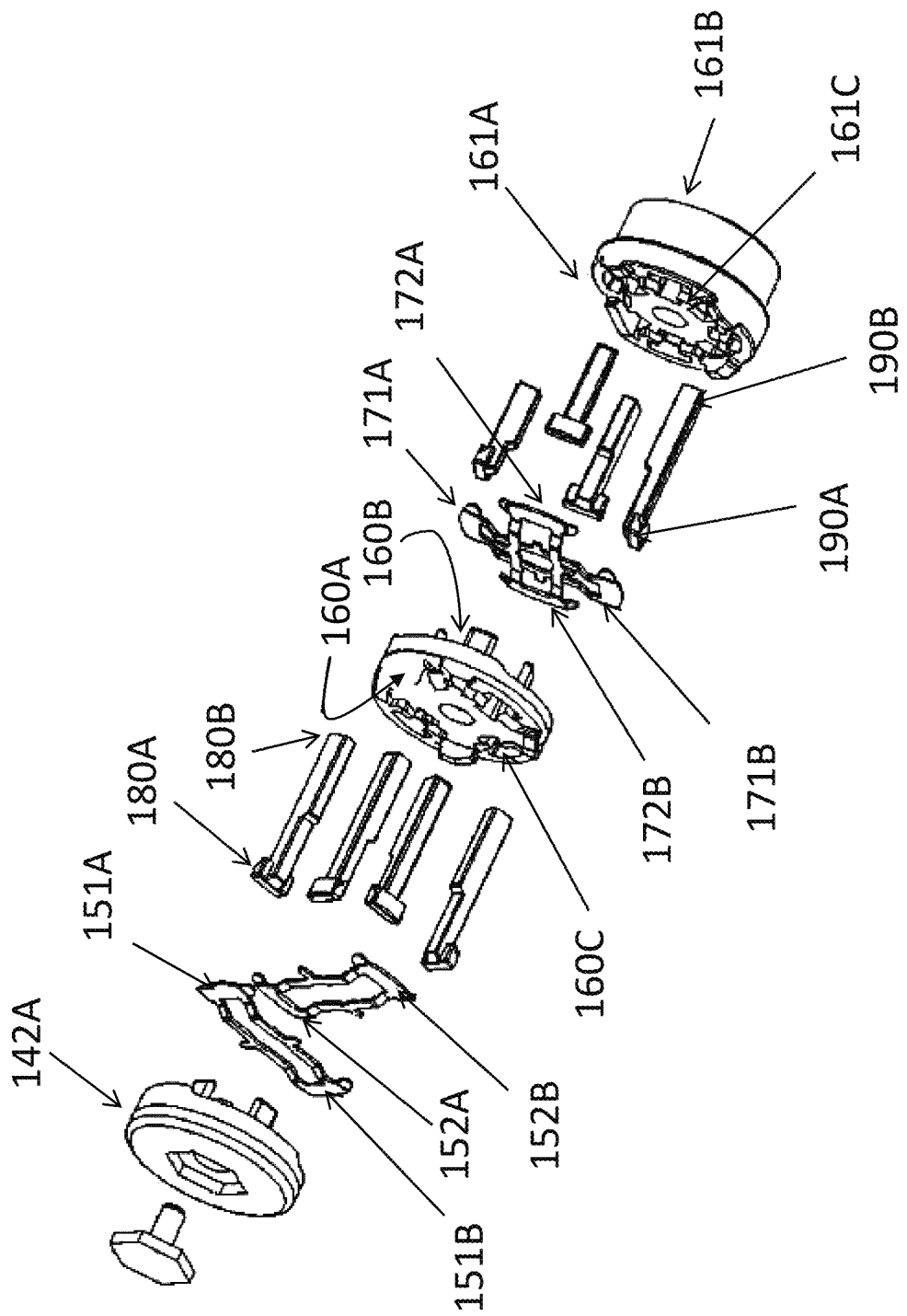
FIG. 4 shows an enlarged view of the clamping head having 2 clamping units of FIG. 3.

FIG. 3 shows an exploded view of clamping head 100 of the present disclosure, which has two sets of clamping units that will be explained further below. However, it should be noted that clamping head 100 can also work with one clamping unit or more than two clamping units subject to the requirement in different applications and/or practical considerations. In FIGS. 3 and 4, clamping head 100 comprises stopper nut 141 fixedly connected to axle 120. Clamping head 100 also has stopper plate 142 fixedly connected to axle 120 such that stopper plate 142 rotates with respect to axle 120. Stopper plate 142 has a first stopper plate surface and a second stopper plate surface which oppose the first stopper plate surface. The first stopper plate surface faces towards stopper nut 141 while second stopper plate surface faces towards motor 40. The second stopper plate surface provides stopper plate clamping surface 142A at the circumference of the second stopper plate surface. Stopper plate 142 can be made of any materials. Preferably, stopper plate 142 is made of plastic.

Clamping head 100 has a first clamping unit including a plurality of spring plates which are arranged adjacent to stopper plate 142. In FIGS. 3 and 4, clamping head 100 has two spring plates 151 and 152 intersecting with each other on a plane of intersection traversing axle 120, that is, rotational axis of stopper plate 142. The first clamping unit is arranged adjacent to stopper plate 142 such that stopper plate clamping surface 142A opposes first spring plate clamping surfaces 151A and 152A of spring plates 151 and 152, respectively. Preferably, two intersect orthogonally to each other which are shown in FIG. 3, though spring plates 151 and 152 could intersect at any angle desired that could allow this invention to work, for example 45 or 60 degrees. It should be understood that the first clamping unit can have a third and a fourth spring plates as desired. In manufacturing, each of the spring plates can be made of any materials, preferably, metal or flexible plastics. Advantageously, spring plates made in metal can provide higher clamping capability for clamping hair. In FIG. 4, spring plates 151 and 152 of the first clamping unit have first spring plate ends which provide first spring plate clamping surfaces 151A and 152A on spring plates 151 and 152, respectively. Spring plates 151 and 152 also have second spring plate clamping surfaces 151B and 152B which are opposite to first spring plate clamping surfaces 151A and 152A, respectively, on respective second spring plate ends of spring plates 151 and 152.

Spaces for clamping hair are formed between the first spring plate clamping surfaces and the stopper plate clamping surface 142A, and the space is used for clamping and then removing hair. Clamping head 100 in FIGS. 3 and 4 has a first space; a second space; a third space; and a fourth space between spring plate clamping surfaces 151A, 151B, 152A, and 152B of the first clamping unit, respectively, and stopper plate clamping surface 142A. Spring plate clamping surface(s) are biased by respective spring plates to engage stopper plate clamping surface 142A to close their respective space (s). Alternatively, spring plate clamping surface(s) are biased by respective spring plates to disengage stopper plate clamping surface 142A to open their respective space(s).

Clamping head 100 shown in FIGS. 3-4 has middle plate 160 arranged coaxially with stopper plate 142. Middle plate 160 has first middle plate surface 160A facing stopper plate clamping surface 142A and an opposing second middle plate surface. Second middle plate surface 160B faces towards motor 40. Middle plate 160 has a plurality of actuator apertures 160C for guiding corresponding actuators 180 to extend through middle plate 160.

Clamping head 100 further comprises a secondary clamping unit which has the same construction as the first clamping unit. The secondary clamping unit has secondary spring plates 171 & 172 which are intersected with each other on the plane of intersection traversing axle 120, that is, rotational axis of stopper plate 142. The secondary clamping unit is arranged adjacent to middle plate 160. Second middle plate surface 160B opposes secondary first spring plate clamping surfaces 171A and 172A of secondary spring plates 171 and 172, respectively. In FIG. 4, secondary spring plates 171 and 172 of the secondary clamping unit have secondary first spring plate ends which provide secondary first spring plate clamping surface 171A and 172A on secondary spring plates 171 and 172, respectively. Secondary spring plates 171 and 172 also have secondary second spring plate clamping surfaces 171B and 172B which are opposite to secondary first spring plate clamping surfaces 171A and 172A, respectively, on respective ends of secondary spring plates 171 and 172.

Space are formed between the secondary spring plate clamping surfaces and the second middle plate surface 160B, and the space is used for clamping hair that will be clamped. Clamping head 100 in FIGS. 3 and 4 has a fifth space; a sixth space; a seventh space; and an eighth space between secondary spring plate clamping surfaces 171A, 171B, 172A, and 172B of the secondary clamping unit, respectively, and second middle plate surface 160B. Spring plate(s) 171 and/or 172 is/are biased to enable their respective clamping surface(s) to engage with second middle plate surface 160B to close their respective space(s) to prevent dust or small particles trapped therein. Alternatively, it can be seen that the spring plate(s) is/are be biased to enable their respective spring plate clamping surface(s) to disengage with second middle plate surface 160B to open their respective space(s).

Clamping head 100 further comprise an actuating unit having a plurality of actuators 180 and 190, end plate 161, and base member 162. As shown in FIGS. 3 and 4, each of actuators 180 and 190 is arranged along the axis of rotation of stopper plate 142. First actuator ends 180A and 190A are adjacent to spring plate clamping surfaces 151A, 152A, 151B, 152B of the first clamping unit and spring plate clamping surfaces 171A, 172A, 171B, 172B of the secondary clamping unit, respectively. Actuators 180 and 190 are in a form of rod-like pin made of plastic. Alternatively, actuators 180 and 190 may be made of metal. End plate 161 is fixedly connected to axle 120 such that end plate 161 rotates about axle 120. End plate 161 has a plurality of actuator apertures 161C on its surface. The position of the plurality of actuator apertures 161C corresponds to the plurality of actuators 180 and 190 such that second actuator ends 180B and 190B extend through actuator apertures 161C of end plate 161 towards base member surface 162A. Base member 162 is arranged on axle 120 and has a fixed angular position about axle 120. When gears 130A, 130B, and 130C rotate, base member 162 does not rotate about axle 120. Base member 162 has a base member surface 162A on which has base member actuating portion 162B. Preferably, base member actuating portion 162B is an axial protrusion, as shown in FIGS. 3 and 4, protruded from base member surface 162A towards stopper plate clamping surface 142A. The configuration of base member actuating portion 162B is an axial protrusion protruded from base member surface 162A. Referring to FIGS. 3 and 4, base member actuating portion 162B has a design having a central plateau portion and two ramps sections arranged at the sides of the plateau portion, however such design is not limiting and any other design which can actuate actuator also fall within the gist of this invention.

When users switch on epilator 1, motor 40 to rotate axle 120 by means of shaft 1 110A, connector 110B, bushing 110C, shaft 2 110D and the gear unit (130A, 130B, and 130C). Since end plate 161, middle plate 160, stopper plate 142, and stopper nut 141 are fixedly connected to axle 120, end plate 161, middle plate 160, stopper plate 142, and stopper nut 141 rotate about axle 120. As axle 120 rotates, spring plates 151, 152, 171, and 172 of the two clamping units also rotates about axle 120. Opening and closing of spaces between stopper plate clamping surface 142A and the spring plate clamping surfaces of the first clamping unit or second middle plate surface 160B and the secondary spring plate clamping surfaces of the secondary clamping unit clamp hair will be described below.

When stopper plate 142 rotates about the axis of rotation, actuators 180 and 190 also rotate, the second actuator end 180B or 190B of each of said plurality of actuators 180 & 190 take turn to push base member actuating portion 162B on base member surface 162A towards resilient member 163. When one of the second actuator ends 180B or 190B moves along the ramp portion of base member actuating portion 162B towards the plateau portion of base member actuating portion 162B, space corresponding to said second actuator end opens. When one of the second actuator ends 180B or 190B is in contact with base member actuating portion 162B, said second actuator end pushes base member 162 towards resilient member 163 thus compresses resilient member 163. When said second actuator end moves downwards to the ramp portion, the compressed resilient member 163 expands and pushes base member 162 towards stopper plate 142, and thus pushing said second actuator end towards stopper plate clamping surface 142A. Expansion of resilient member 163 provides a clamping force to close the respective spaces between stopper plate clamping surface 142A and the spring plate clamping surfaces of the first clamping unit, or second middle plate surface 160B and the secondary spring plate clamping surfaces of the secondary clamping unit.

Alternatively, the opening and closing of the space(s) can be realized below. When stopper plate 142 rotates about the axis of rotation, actuators 180 & and 190 also rotate, resilient member 163 moves reciprocally towards and away from base member 162 to push base member 162, thus base member actuating portion 162B of base member 162 pushes second actuator end 180B and/or 190B to move towards stopper plate clamping surface 142A to close the space(s). As such, hair will then be depilated from skin along with the rotation of the respective spaces about axle 120 when the hair is trapped therein. After the second actuator end pushed base member actuating portion 162B, the space will open again. During rotation of the stopper plate 142, clamping unit(s) reciprocally move(s) away from and towards the stopper plate 142 such that space(s) reciprocally open(s) and close(s), respectively, for clamping hair.

Figure 5:
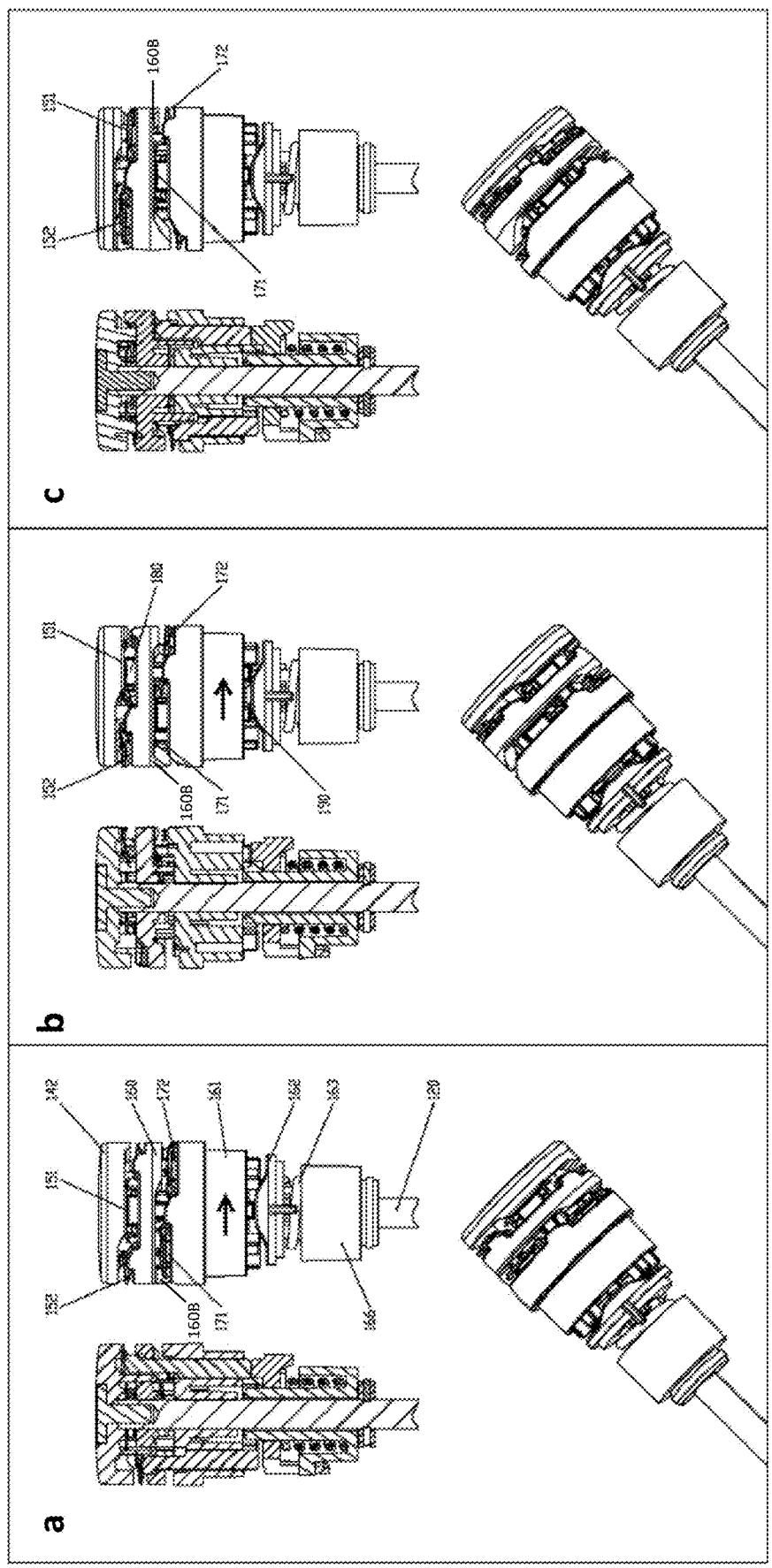
FIGS. 5a to 5c are schematic diagrams showing the movement of spring plates when respective actuators are in contact with the base member actuating portion of the base member during rotation.

The rotation of components such as stopper plate 142, middle plate 160, end plate 161, and spring plates 151, 171, 172 with respect to axle 120 is shown in more detail in FIG. 5. As shown in FIG. 5A, when one of the actuators of spring plate 151 is in contact with base member actuating portion 162B of base member 162, spring plate 151 engages stopper plate 142. Meanwhile, when other actuators of spring plates 171 and 172 are not in contact with base member actuating portion 162B of base member 162, spring plates 171 and 172 are biased away from the second middle plate surface 160B. FIG. 5B shows the state when axle 120 rotates 22.5° with respect to the configuration in FIG. 5A. In FIG. 5B, the actuator of spring plates 151 moves downwards along the ramp of base member actuating portion 162B of base member 162. Since the actuator end of the spring plate 151 remains in contact with base member actuating portion 162B of base member 162, spring plate 151 remains biasing towards stopper plate 142. Meanwhile, one of the actuators of spring plate 171 moves upwards along the ramp portion of base member 162 towards the plateau portion of base member 162, thus spring plate 171 engages second middle plate surface. Since actuator of spring plate 172 disengages with base member actuating portion 162B of base member 162, spring plate 172 also remains disengaged with second middle plate surface 160B. FIG. 5C shows the state when axle 120 rotates 22.5° with respect to the configuration in FIG. 5B. In FIG. 5C, one of the actuator of spring plate 171 is in contact with base member actuating portion 162B of base member 162, thus spring plate 171 clamps second middle plate surface 160B. Meanwhile, actuators of spring plates 151 and 172 moves away from base member actuating portion 162B of base member 162, spring plates 151 and 172 are biased away from stopper plate 142 and the second middle plate surface, respectively.

Figures 7A, 7B, 7C:
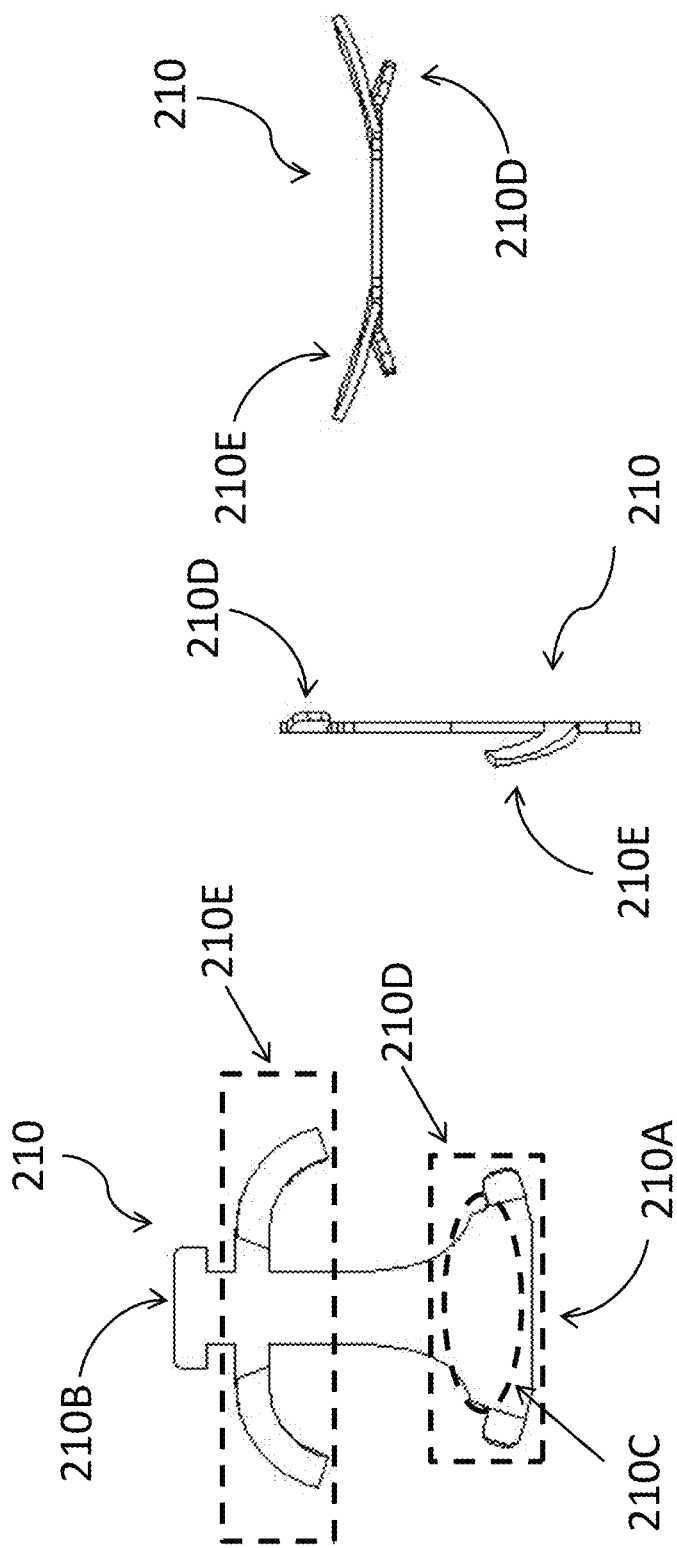
FIG. 7a-7c show the respective views of spring plate 210 when such is viewed from angles A, B, and C of FIG. 6, respectively.

FIG. 6 shows a perspective view of spring plate 210 of the second embodiment of this invention, which is different from spring plates 151 & 171 of the first embodiment. FIGS. 7a-7c show different views of spring plate 210 when viewing the spring plate 210 of FIG. 6 from different angles, i.e. angles A-C, respectively, in FIG. 6. As shown in FIG. 7a, spring plate 210 shapes as an "anchor" having a first spring plate end 210A and a second spring plate end 210B opposing the first spring plate end 210A, though spring plate 210 has an anchor shape is not absolutely necessary. Any shape of spring plate such as rectangular, trapezium, or irregular shape, as long as spring plate provide an end capable of clamping hair. FIG. 7a shows that first spring plate end 210A provides first spring plate clamping surface 210C which shown in a dotted circle in FIG. 7a. FIG. 7a also shows that first spring plate end 210A has a first pair of wings 210D on spring plate 210 (shown in a dotted rectangle in FIG. 7a), and second spring plate end 210B has a second pair of wings 210E on spring plate 210 (shown in a dotted rectangle in FIG. 7a). As shown in FIGS. 7b and 7c, first pair of wings 210D are biased to a first direction from spring plate 210 and second pair of wings 210E are biased to a second direction from spring plate 210, wherein the first direction opposes the second direction. Spring plates 210 can be made of any materials, preferably, metal or flexible plastics. Advantageously, spring plates 210 made of metal, but also could be made of other materials with elasticity like plastic.

Figure 8:
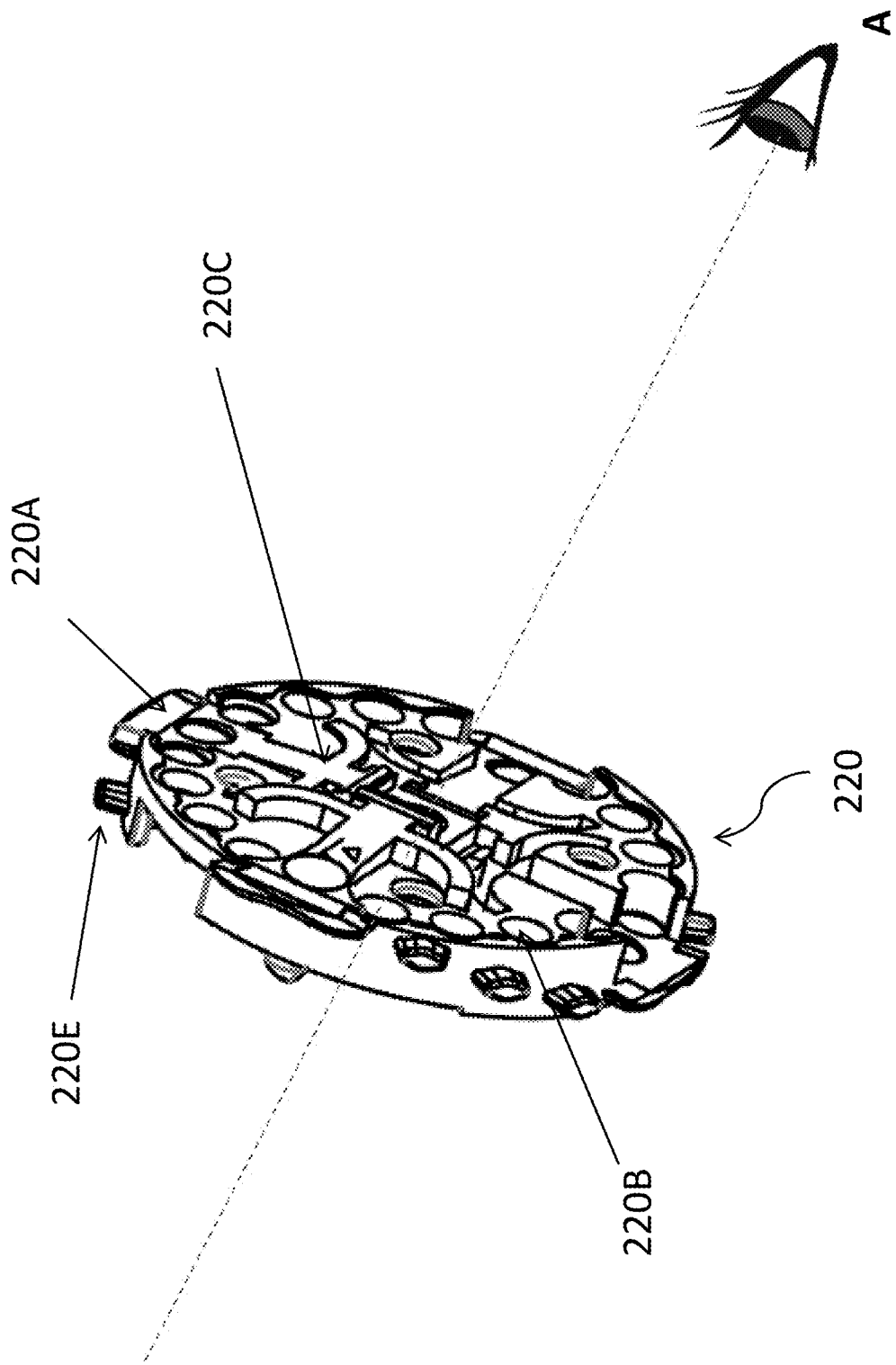
FIG. 8 shows a perspective view of stopper plate 220 of the second embodiment of this invention.
Figure 9:
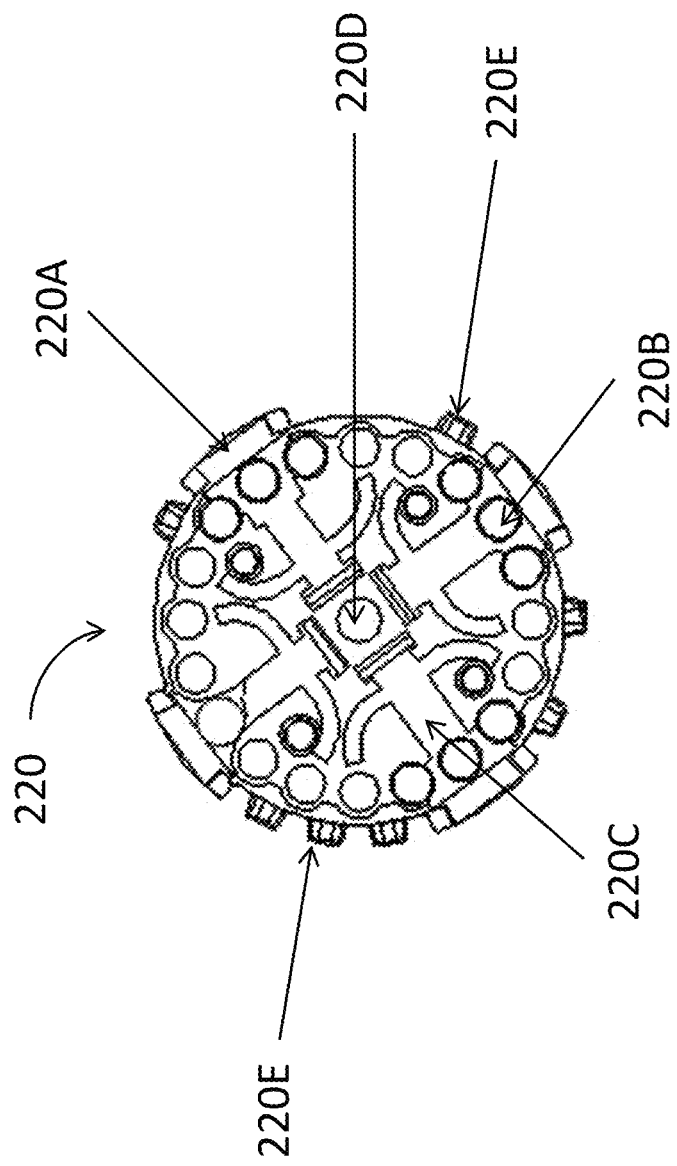
FIG. 9 shows the respective views of stopper plate 220 when such is viewed from angle A of FIG. 8.

FIG. 8 shows a perspective view of stopper plate 220 of the second embodiment of this invention, which is different from stopper plate 142 of the first embodiment. FIG. 9 shows the view when the stopper plate 220 of FIG. 8 is viewed from angle A in FIG. 8. In FIG. 9, stopper plate 220 has an axle aperture 220D at the center of stopper plate 220 allowing an axle (will be shown later) to pass through. Stopper plate 220 has a plurality of actuator aperture 220B at the perimeter of stopper plate 220 allowing actuators (will be shown later) to pass through. The position of actuator aperture 220B can deviate from the perimeter of stopper plate 220 to an extent that when spring plate 210 is biased by actuator, engaging and/or disengaging between first spring plate clamping surface 210C and stopper plate clamping surface (will be shown later) can still clamp hair. The aperture size of each actuator aperture 220B should be large enough to allow actuator (will be shown later) to pass through actuator aperture 220B. The number of actuator aperture 220B at the perimeter of the stopper plate 220D is limited by the area of stopper plate 220D, otherwise could be any desired number. To relieve pain hair epilation, the rim of stopper plate 220 could have a plurality of protrusions 220E for massaging the user. The number of stopper plate clamping surface 220A on stopper plate 220 corresponds to the number of first spring plate clamping surface 210C of spring plate 210 as shown in FIG. 6. Stopper plate clamping surface 220A is at the perimeter of stopper plate 220, or stopper plate clamping surface 220A cannot be used to clamp hair if the stopper plate clamping surface 220A is at elsewhere. The position of stopper plate clamping surface 220A can deviate from the perimeter of stopper plate 220 to an extent that when spring plate 210 is biased by actuator, engaging and/or disengaging between first spring plate clamping surface 210C and stopper plate clamping surface can still clamp hair.

FIG. 9 also shows that stopper plate 220 has recesses 220C in "anchor" shape complementary to the shape of spring plate 210, that is, anchor shape as shown in FIG. 6. Naturally, the number of recess 220C on stopper plate 220 corresponds to the number of spring plates 210 on the same stopper plate 220. Alternatively, the shape of recess 220C can be any shape as long as recess 220C can accommodate spring plate 210. Although the number of recess 220C of stopper plate 220 are four in FIG. 9, however these are just examples, which could be decided based on the ratio between the area of stopper plate to the area of spring plate.

Figure 10:
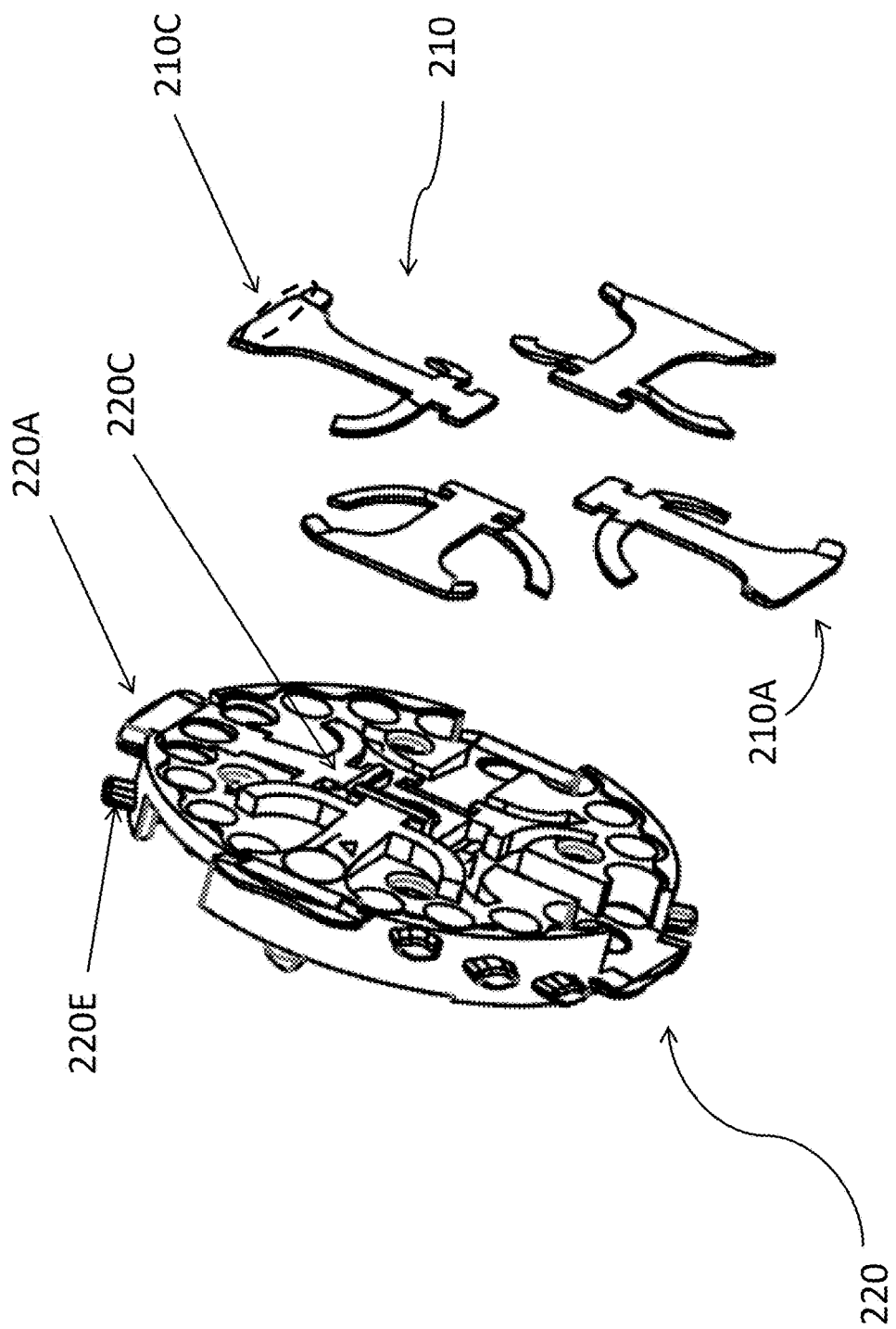
FIG. 10 shows an enlarged view of stopper plate 220 having a stopper plate clamping surface 220A adjacent to spring plates 210 having first spring plate clamping surface 210C.

As shown in FIG. 10, recesses 220C of stopper plate 220 accommodate spring plates 210. Each spring plate 210 in FIG. 10 is able to be biased by respective actuator, which will be explained in details later, to allow first spring plate clamping surface 210C of spring plate 210 engaging or disengaging with stopper plate clamping surface 220A of stopper plate 220. When first spring plate clamping surface 210C of spring plate 210 disengages with stopper plate clamping surface 220A of stopper plate 220, a space is formed between the stopper plate clamping surface 220A of stopper plate 220 and first spring plate clamping surface 210C of spring plate 210. When first spring plate clamping surface 210C of spring plate 210 engages with stopper plate clamping surface 220A of stopper plate 220, the space between the stopper plate clamping surface 220A of stopper plate 220 and first spring plate clamping surface 210C of spring plate 210 closes.

Figure 11:
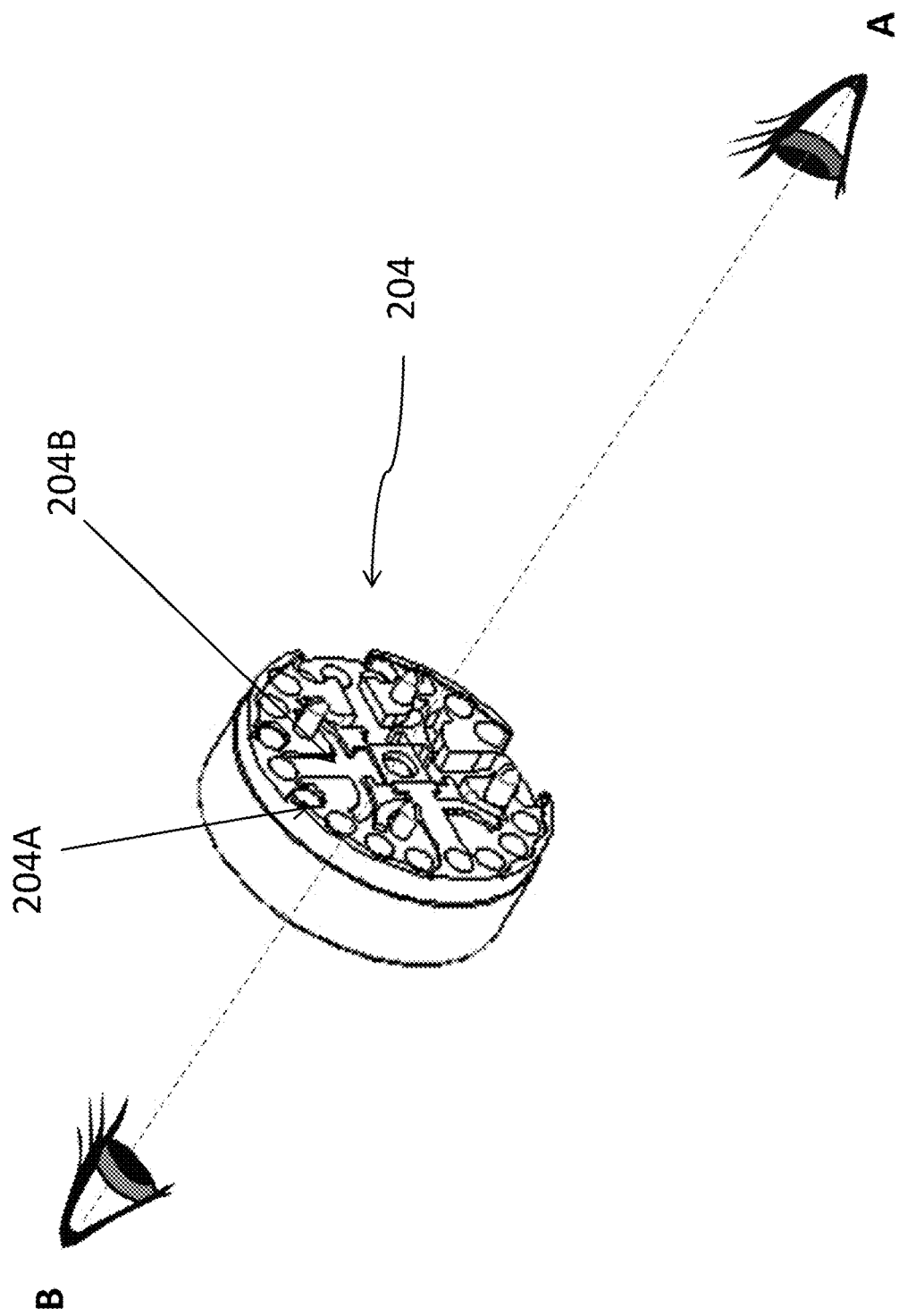
FIG. 11 shows a perspective view of end plate 204 of the second embodiment of this invention.

FIG. 11 shows a perspective view of end plate 204 of the second embodiment of this invention, which is different from end plate 161 of the first embodiment. FIGS. 12a and 12b show the view of end plate 204 of FIG. 11 from angles A and B, respectively. FIG. 11 shows that end plate has certain thickness to accommodate gears and actuators, which will be shown in more detail in FIG. 16. FIG. 12a shows that end plate 204 resembles stopper plate 220 shown in FIG. 9, except end plate 204 does not have any clamping surface at the peripheral. Therefore, description on end plate 204 is also applicable to stopper plate 220. However, end plate 204 can also have clamping surface as stopper plate 220 has clamping surface 220A if desired.

Figure 13B:
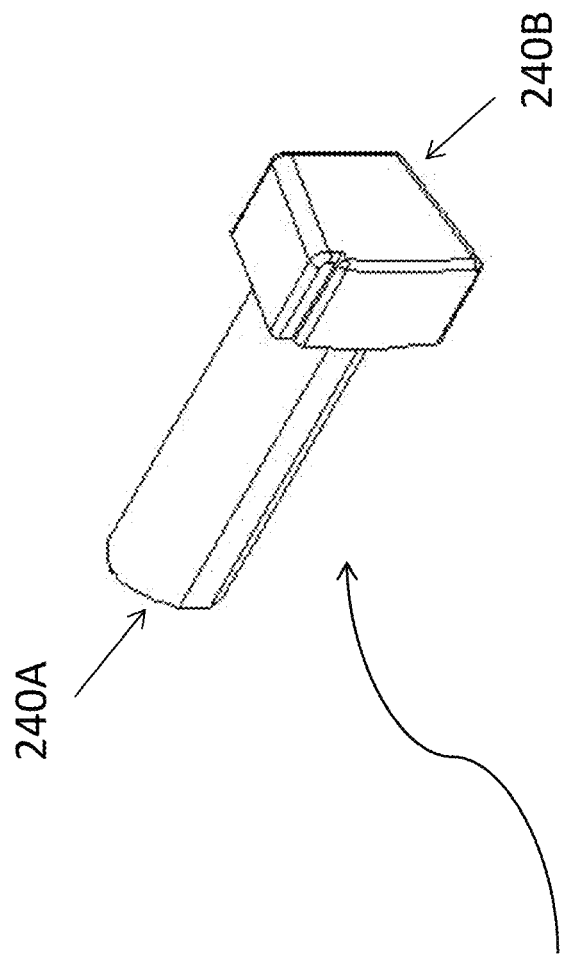
FIGS. 13a to 13b show 2 perspective views of actuator 240 of the second embodiment of this invention.
Figure 13A:
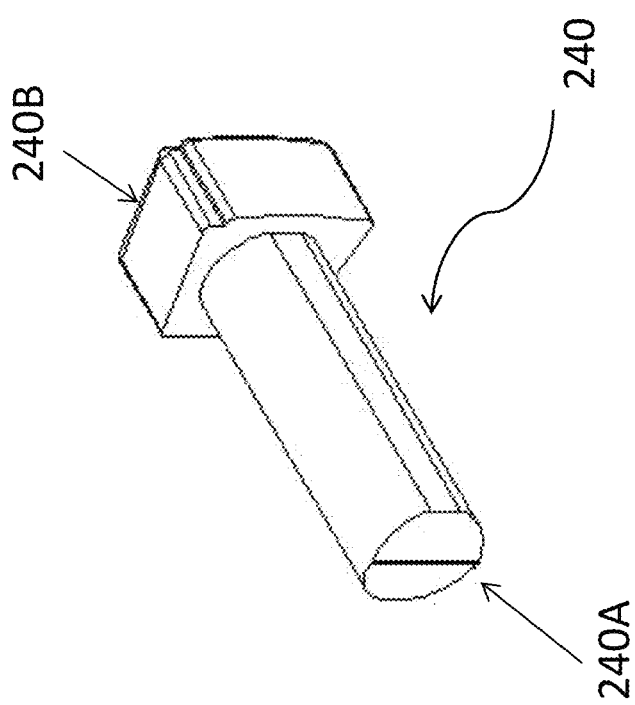
Figure 13C:
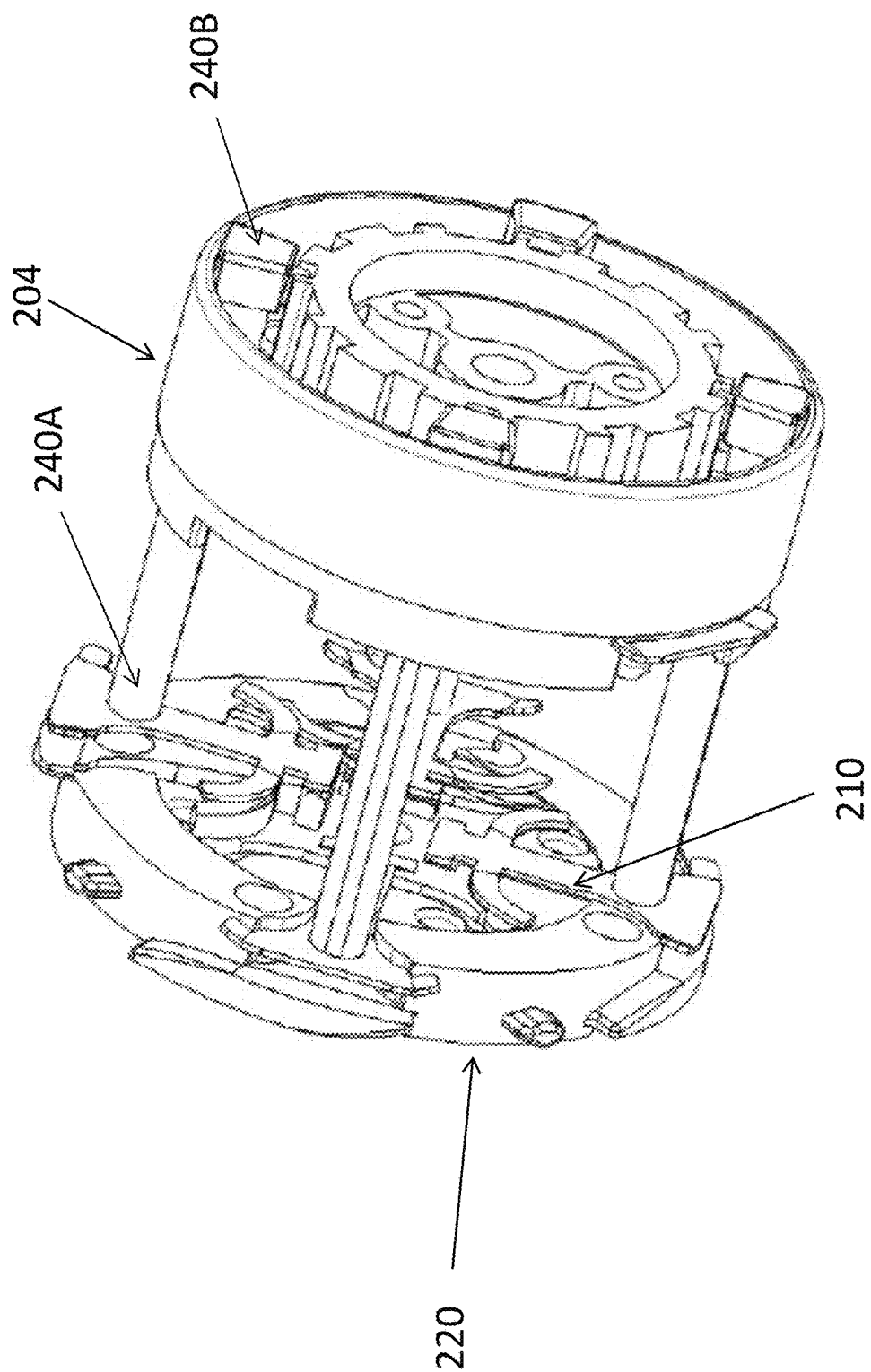
FIG. 13c shows an assembly having a plurality of actuators on end plate 204 which is adjacent to spring plates 210 on stopper plate 220.

FIGS. 13a-13b show an actuator 240 of the second embodiment of this invention, which is different from actuators 180 and 190 of the first embodiment. However, actuators 240, 180, and 190 could also be the same. As shown in FIGS. 13a and 13b, actuator 240 has a first actuator end 240A and a second actuator end 240B opposing the first actuator end 240A. First actuator end 240A extends through a plurality of actuator apertures 204A of end plate 204 which will be shown in details in FIG. 16. The cross section area of first actuator end 240A of actuator 240 is circular, though the cross section can be square, triangular, pentagonal, polyhedron, or even irregular shape. Preferably, the cross section of second actuator end 240B of actuator 240 is larger than that of first actuator end 240A of actuator 240, but this could be reversed. The cross section area of second actuator end 240B of actuator 240 has a trapezium shape, though a trapezium shape is not absolutely necessary to be the cross section area of second actuator end 240B of actuator 240. The cross section of the second actuator end 240B of actuator 240 can be square, triangular, pentagonal, polyhedron, or even irregular shape. Advantageously, an assembly of a plurality of actuators 240 at second actuator ends 240B of actuators 240 forms an actuating unit as shown in FIG. 13c and operation of the actuating unit will be set forth in FIG. 16. In FIG. 13c, four actuators 240 with the same length are assembled on end plate 204, wherein first actuator end 240A of each actuator 204 passes through their respective actuator apertures 204A of end plate 204 to engage/disengage spring plates 210 which have also been assembled on recess 220C of stopper plate 220. The length of actuators 240 in FIG. 13c are the same, however, when a clamping head comprises a plurality of stopper plates and spring plates, the length of each actuator 240 in an actuating unit can be different, which will be shown in FIG. 22.

Figure 14:
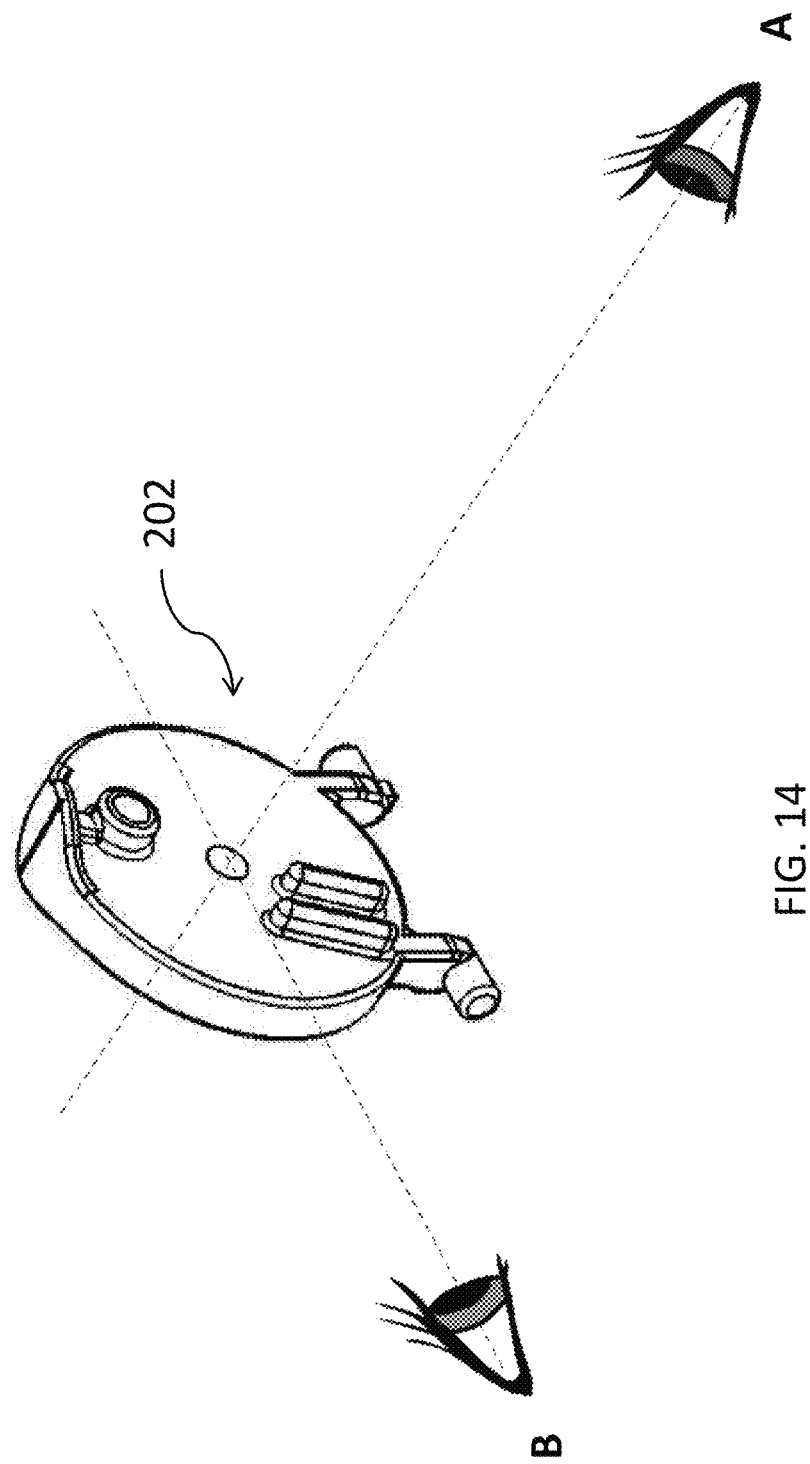
FIG. 14 shows a perspective view of base member 202 of the second embodiment of this invention.
Figure 15B:
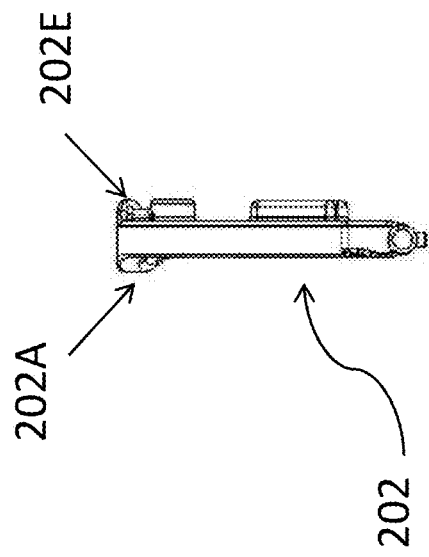
FIGS. 15a to 15b show the respective views of base member 202 when such is viewed from angles A to B of FIG. 11, respectively.
Figure 15A:
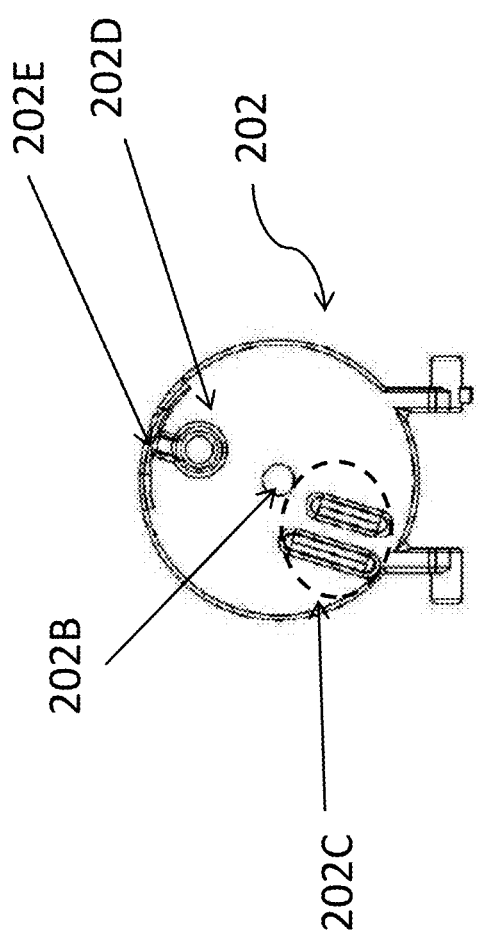

FIG. 14 shows a perspective view of base member 202 of the second embodiment of this invention, which is different from base member 162 of the first embodiment. FIGS. 15a-15b shows the views of base member 202 of FIG. 14 from angles A and B, respectively. FIG. 15a shows that base member 202 has an axle aperture 202B allowing an axle (will be shown later) to pass through. FIG. 15a also shows that base member 202 has guiding track 202C (shown in dotted circle), first axial protrusion 202D, and second axial protrusion 202E. The guiding track 202C, first axial protrusion 202D, and second axial protrusion 202E are used to assemble a clamping head having plurality of repeating units of stopper plate 220, spring plate 210, and other components, for example in FIGS. 22 and 23 that will be shown later. However, guiding track 202C, first axial protrusion 202D, and second axial protrusion 202E are not absolutely necessary to be presented on base member 202. FIG. 15b shows a base member actuating portion 202A on base member surface of base member 202. The base member actuating portion 202A of base member 202 has the same function of the base member actuating portion 162B of base member 162 of the first embodiment, wherein the base member actuating portion 202A has a central plateau portion and two ramps sections arranged at the sides of the plateau portion.

Figure 16:
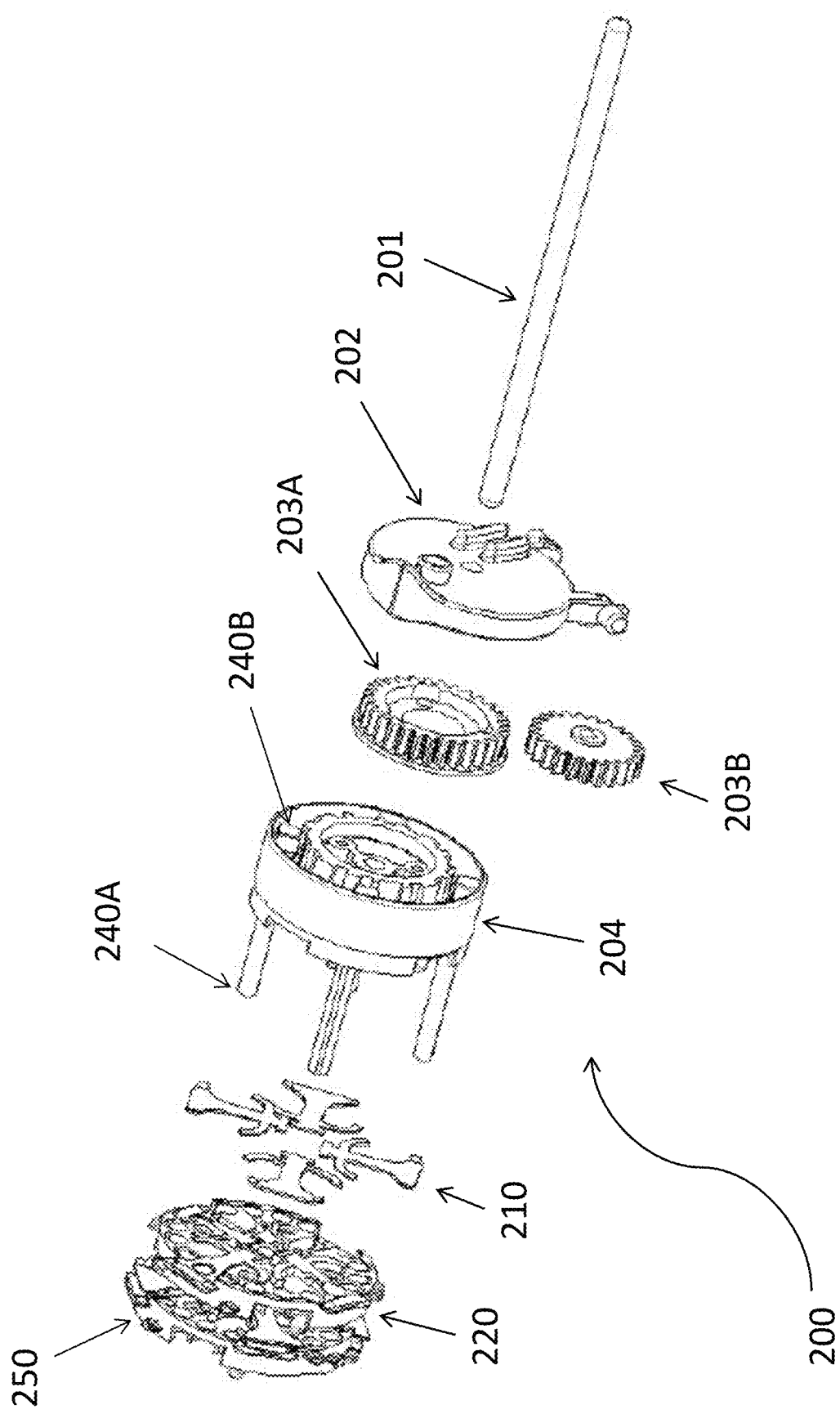
FIG. 16 shows an exploded view of a clamping head 200 of a second embodiment.

FIG. 16 shows an exploded view of the second embodiment of clamping head 200 of the present invention. In FIG. 16, the clamping head 200 comprises first gear 203A, second gear 203B, a base member 202, an actuating unit having a plurality of actuators 240, an end plate 204, a cover plate 250 and an axle 201. As shown in FIG. 16, cover plate 250 in FIG. 16 is an outer part of the clamping head 200, and four spring plates 210 are arranged on a plane traversing an axis of rotation coinciding with axle 201. Each spring plate 210 is sandwiched between recess 220C of stopper plate 220 (as shown in FIG. 9) and recess 204B of end plate 204 (as shown in FIG. 15). When the epilator in FIG. 16 is turned on, first gear 203A and second gear 203B are driven by a motor (not shown) to rotate. Meanwhile, end plate 204, spring plates 210, stopper plates 220 are also rotated while base member 202 is stationary with respect to axle 201, that is, base member 202 do not rotate when first gear 203A and second gear 203B rotate. First actuator end 240A of actuator 240 extends through the end plate 204 via the corresponding actuator apertures 204A to push corresponding spring plate 210.

Figure 17:
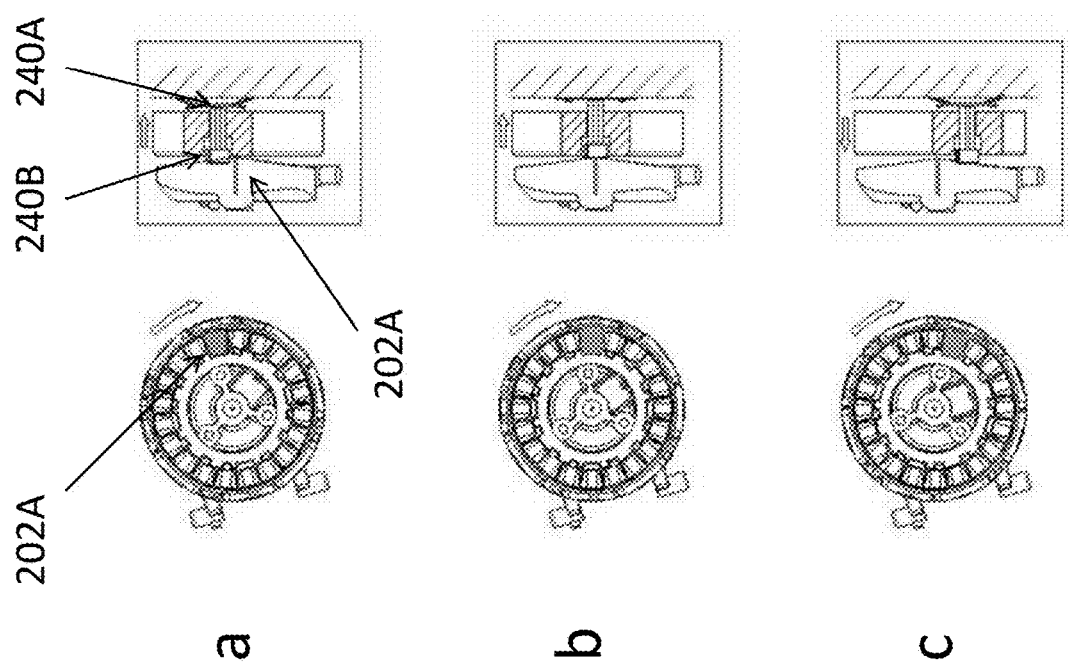
FIGS. 17a to 17c are schematic diagrams showing the clamping of spring plate 210 in response to the movement of one of the actuators 240 during rotation of the actuators 240 about axle 201.

In FIG. 17a, during rotation of axle 210, actuator end 240B of one actuator disengages with base member actuating portion 202A on base member surface of base member 202, the space corresponding to actuator end 240B opens. In FIG. 17b, when actuator end 240B' of adjacent actuator just disengaged with base member actuating portion 202A, this actuator end 240B' engages with base member actuating portion 202A of base member 202, and spring plate corresponding to said actuator end 240B is biased to close the corresponding space. In FIG. 17c, when actuator end 240B' disengaged with base member actuating portion 202A, spring plate corresponding to actuator end 240B' is biased to open said corresponding space again as shown. During rotation of axle 210, each second actuator end 240B takes turn to push base member actuating portion 202A of base member 202 to close corresponding space for clamping hairs.

Figure 18:
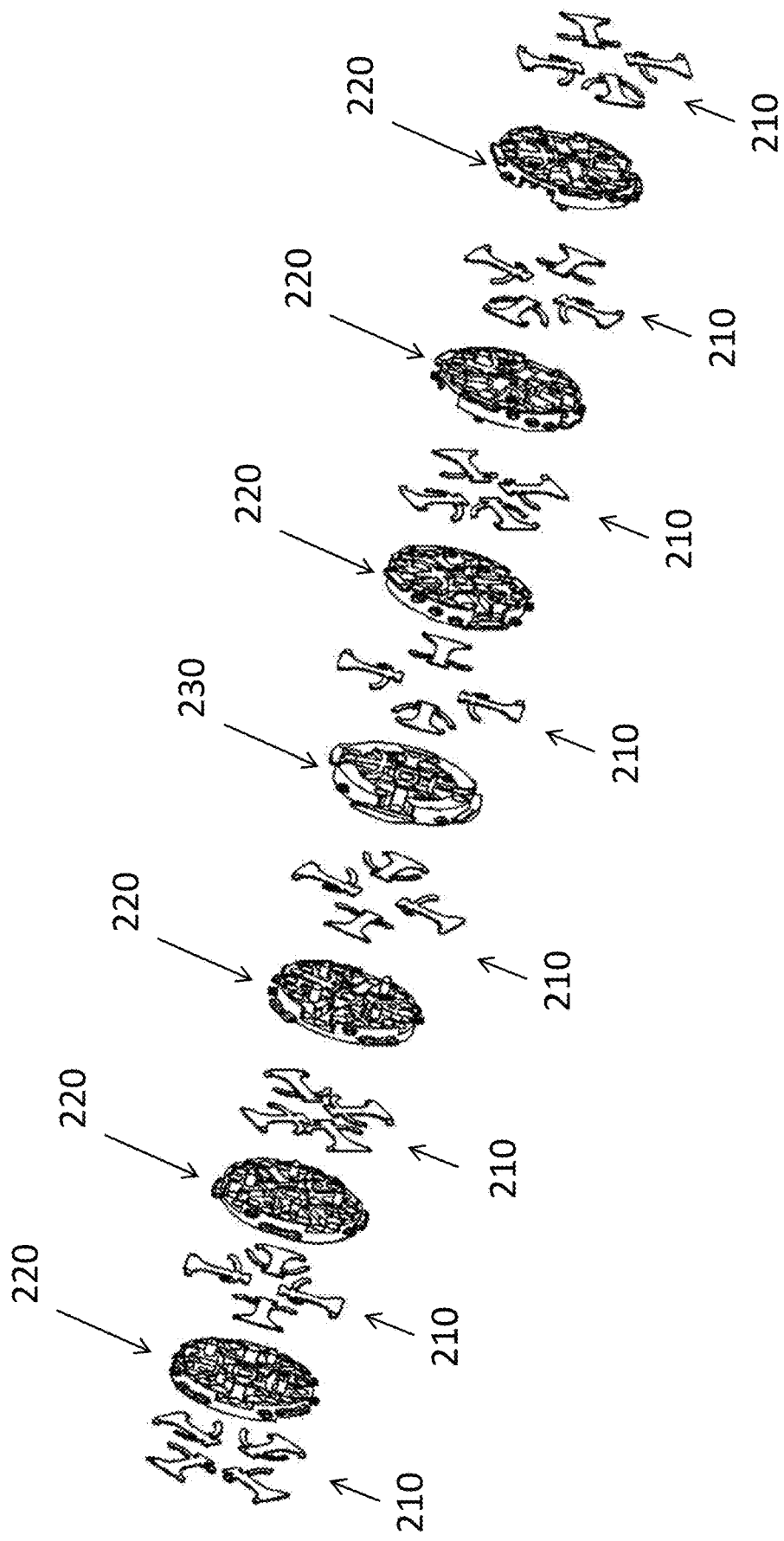
FIG. 18 shows repeating units of spring plates 210 and repeating units of stopper plates 220 and a middle plate 230.

FIG. 18 shows an embodiment of this invention with repeating units of spring plates 210 and repeating units of stopper plates 220 in FIG. 16. This embodiment has an additional middle plate 230 arranged coaxially on an axle (not shown). The number of stopper plate and middle plate can be any number.

Figure 19:
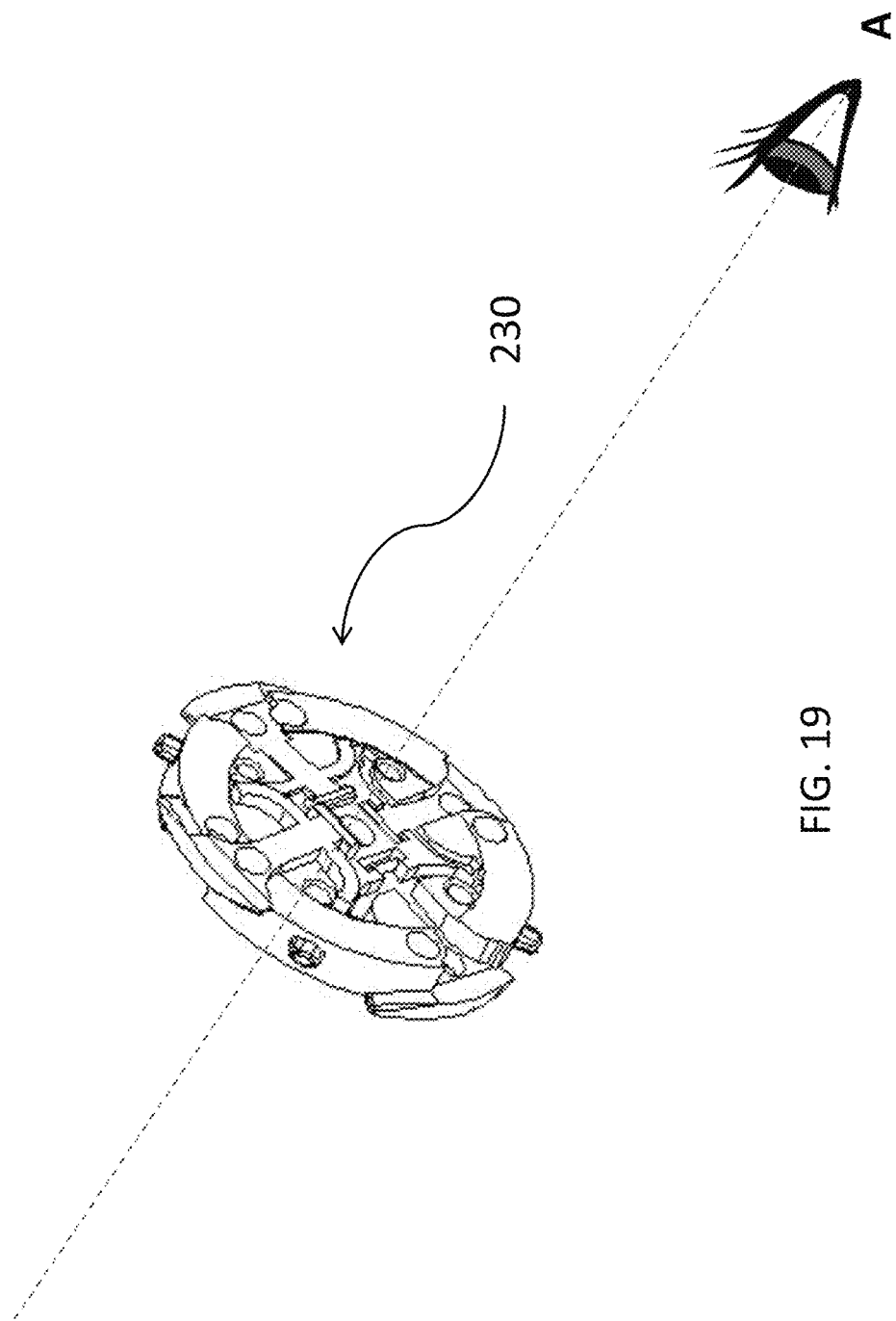
FIG. 19 shows a perspective view of middle plate 230 of the second embodiment of this invention.
Figure 20:
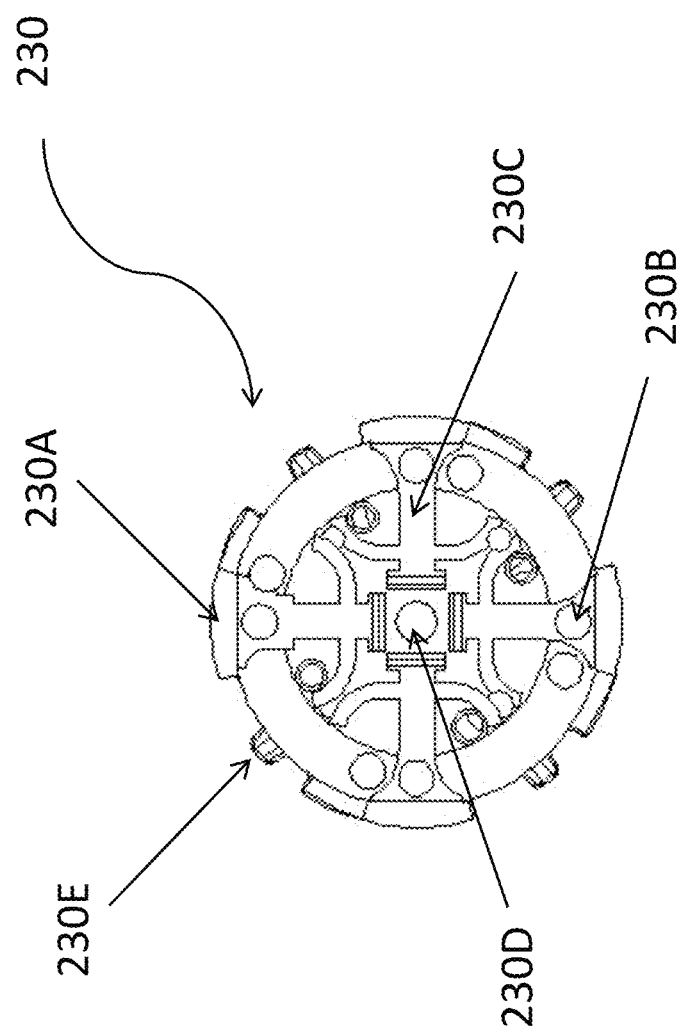
FIG. 20 shows the respective views of middle plate 230 when such is viewed from angle A.
Figure 21:
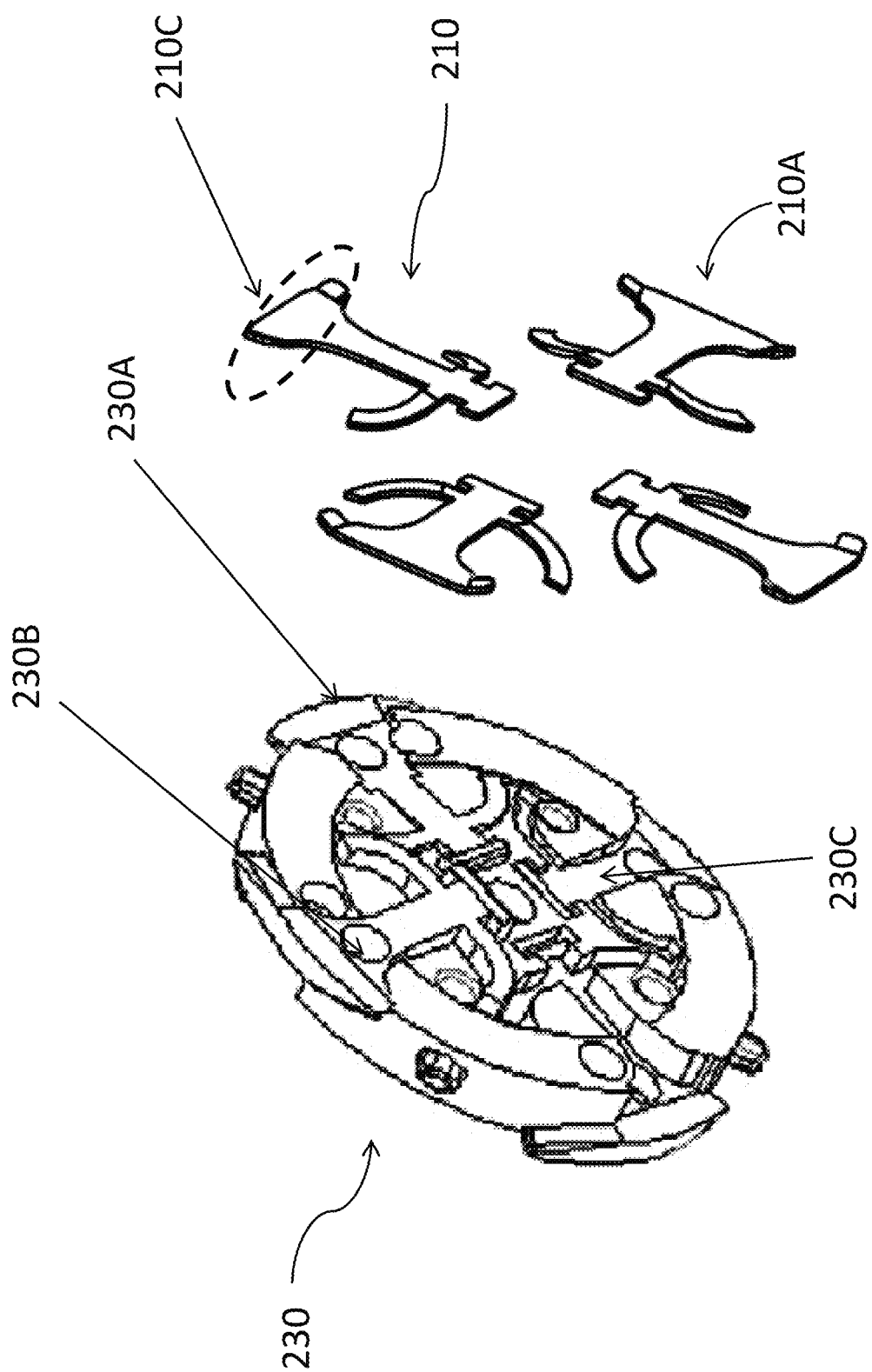
FIG. 21 shows an enlarged view of middle plate 230 having a middle plate clamping surface 230A adjacent to spring plates 210 having first spring plate clamping surface 210C.

FIG. 19 shows a perspective view of middle plate 230 of the second embodiment of this invention, which is different from middle plate 160 of the first embodiment. FIG. 20 shows the the middle plate 230 when view from angle A in FIG. 19, in which middle plate 160 resembles stopper plate 220 shown in FIG. 9. Therefore, description on middle plate 160 is also applicable to stopper plate 220. As shown in FIG. 21, recesses 230C of middle plate 230 accommodate spring plates 210. Each spring plate 210 in FIG. 21 is able to be biased by respective actuator, which will be explained in details in FIG. 22, to allow first spring plate clamping surface 210C of spring plate 210 engaging or disengaging with middle plate clamping surface 230A of middle plate 230. When first spring plate clamping surface 210C of spring plate 210 disengages with middle plate clamping surface 230A of middle plate 230, a space is formed between the middle plate clamping surface 230A of middle plate 230 and first spring plate clamping surface 210C of spring plate 210. When first spring plate clamping surface 210C of spring plate 210 engages with middle plate clamping surface 230A of middle plate 230, the space between the middle plate clamping surface 230A of middle plate 230 and first spring plate clamping surface 210C of spring plate 210 closes.

Figure 22:
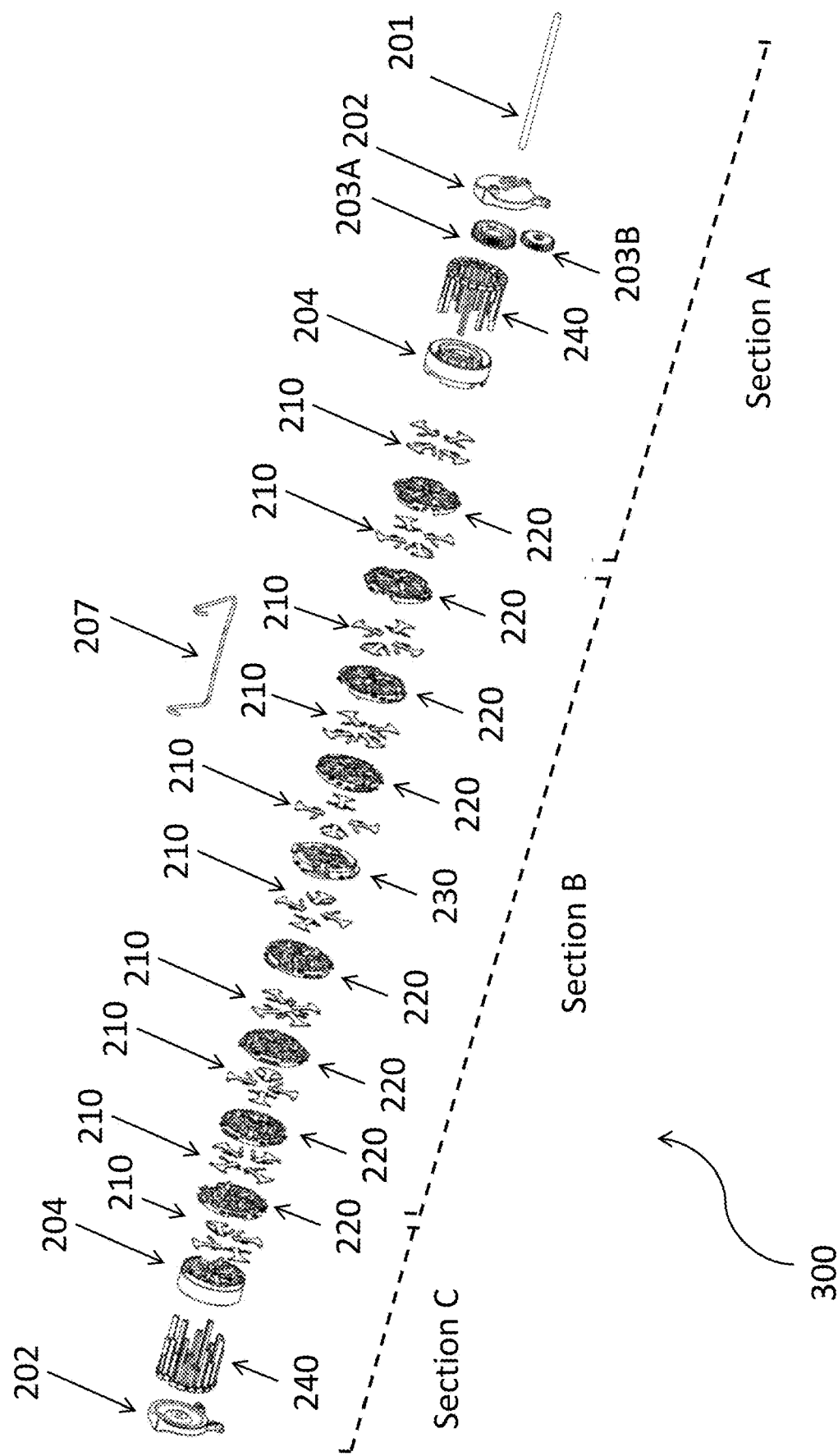
FIG. 22 shows an exploded view of a clamping head 300 of a third embodiment of this invention.
Figure 23:
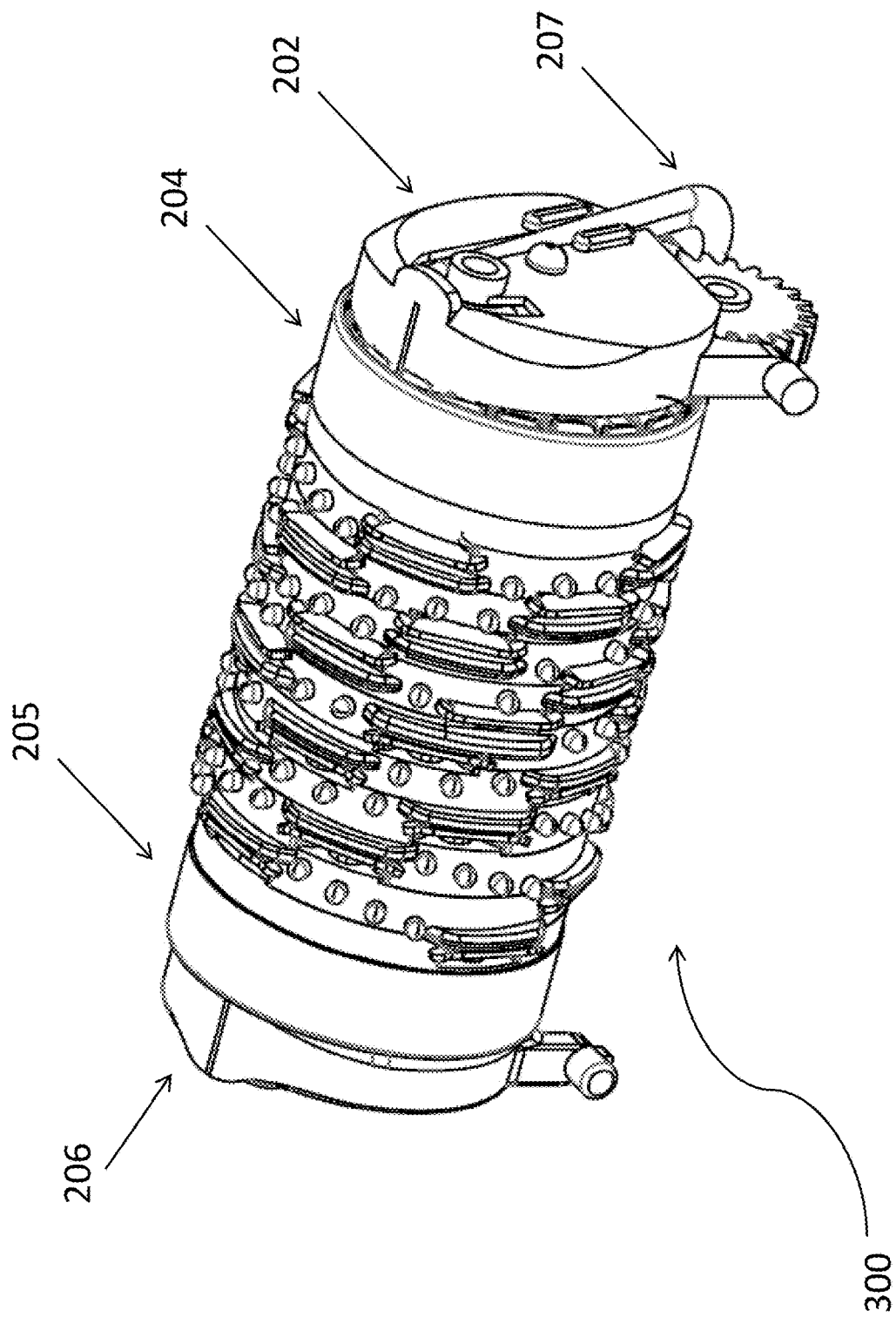
FIG. 23 shows an assembled state of a clamping head 300 shown in FIG. 22.

FIG. 22 shows a third embodiment of this invention, in which clamping head 300 comprises two base members 202, two end plates 204, two sets of actuating units having a plurality of actuators 240, a middle plate 230, eight stopper plates 220, forty spring plates 210. The number and arrangement of middle plate 230, spring plate 210, stopper plate 220, and actuators 240 are merely an example in FIG. 22, while these units could be repeated indefinitely as long as these components can be driven by gears 230A and 230B. FIG. 22 shows that the clamping head 300 has three sections, namely, sections A, B, and C. FIG. 22 shows that the configuration of section C repeats substantially that of section A, but section C does not have first gear 203A, second gear 203B and axle 201. However, section C can also have gears 230A and 230B driven by motor. In FIG. 22, the working and operation mechanism of section C is the same as section A, wherein section A in FIG. 22 is the clamping head 200 of the second embodiment, therefore the working and operation mechanism of section A and section C is the same as that of FIG. 17 described before. When the epilator in FIG. 22 is turned on, first gear 203A and second gear 203B are driven by a motor (not shown) to rotate first gear 203A and second gear 203B. Meanwhile, end plates 204, spring plates 210, stopper plates 220, middle plate 230 are also rotated while base members 202 are stationary with respect to axle 201, that is, base member 202 do not rotate when first gear 203A and second gear 203B rotate. FIG. 22 shows that first actuator end 240A of actuator 240 is able to extend through end plates 204 via the corresponding actuator apertures 204A of end plates 204 to push corresponding spring plate 210 to close corresponding spaces for clamping hair.

This invention uses spring plate to replace coil spring that is used in the state of art in a clamping head. Existing epilator, like the one in US2014309663, uses a plurality of springs to enable clamping elements for clamping, for which the assembly is complex. The use of spring plate in the epilator in this invention could, comparatively, improve durability, ease of assembly, and use less materials.

While preferred embodiments of the present disclosure have been described in detail by the examples, it is apparent that modifications and adaptations will occur to those skilled in the art. Furthermore, the above-described embodiments shall not be interpreted to be restricted by the examples or figures only. It is to be expressly understood, however, that such modifications and adaptations are within the scope of the present disclosure, as set forth in the following claims. For instance, features illustrated or described as part of one embodiment can be used on another embodiment to yield a still further embodiment. Thus, it is intended that the present disclosure cover such modifications and variations as come within the scope of the claims and their equivalents.

The invention claimed is:

1. A clamping head comprising:
    a first clamping unit including at least two spring plates arranged adjacent to each other on a plane traversing an axis of rotation of a stopper plate, each said spring plate has a first spring plate end, comprising a first spring plate clamping surface, and a second spring plate end, opposing the first spring plate end and comprising a second spring plate clamping surface, wherein the first clamping unit does not engage with any coil spring;
    said stopper plate is adjacent to said first clamping unit and having a stopper plate clamping surface opposing said first spring plate clamping surface of each said spring plate;
    during rotation of said stopper plate relative to said first clamping unit, said first clamping unit reciprocally moves away from and towards said stopper plate such that a first space between said first spring plate clamping surface and said stopper plate clamping surface opens and closes for clamping hair.

2. A clamping head according to claim 1, wherein each said spring plate is made of metal.

3. A clamping head according to claim 1, wherein said stopper plate is made of plastic.

4. A clamping head according to claim 1, wherein said first clamping unit has only two said spring plates.

5. A clamping head according to claim 1, wherein said two spring plates intersect orthogonally to each other.

6. A clamping head according to claim 1, wherein the clamping head extends laterally along a handle of an epilator.

7. A clamping head according to claim 1, wherein each said spring plate has a second spring plate end opposing said first spring plate end, said first spring plate end has a first pair of wings on said spring plate, and said second spring plate end has a second pair of wings on said spring plate, wherein said first pair of wings are biased to a first direction and said second pair of wings are biased to a second direction, wherein the first direction opposes the second direction, and wherein the second pair of wings are flexible.

8. A clamping head according to claim 7, wherein said first clamping unit having four said spring plates.

9. A clamping head according to claim 7, wherein the clamping head extends horizontally along a handle of an epilator.

10. A clamping head according to claim 1, wherein at least one of said spring plates is biased to enable said first spring plate clamping surface thereof to engage with said stopper plate clamping surface to close said first space.

11. A clamping head according claim 1, wherein at least one of said spring plates is biased to enable said first spring plate clamping surface thereof to disengage with said stopper plate clamping surface to open said first space.

12. A clamping head according to claim 1, further comprising an actuating unit having:
   a plurality of actuators, each of said plurality of actuators has a first actuator end pointing towards said stopper plate clamping surface and a second actuator end opposing said first actuator end, each of said plurality of actuators being arranged along said axis of rotation;
   an end plate being arranged coaxially with said stopper plate, wherein said end plate has a plurality of actuator apertures corresponding to said plurality of actuators to allow respective said plurality of actuators extending through said end plate; and
   a base member being arranged coaxially with said stopper plate, said base member has a base member surface having an actuating portion, said base member surface facing towards said stopper plate clamping surface.

13. A clamping head according to claim 12, wherein the actuating portion is an axial protrusion protruding from said base member surface towards said stopper plate clamping surface.

14. A clamping head according to claim 13, wherein each of said first actuator ends is disposed adjacent to one of said respective first spring plate ends of each said spring plate of said first clamping unit,
   when said stopper plate rotates about said axis of rotation, said plurality of actuators also rotate about said axis of rotation, said second actuator end of each of said plurality of actuators take turn to push said axial protrusion to move towards said stopper plate clamping surface to close said first space.

15. A clamping head according to claim 12, wherein the actuating portion is a recess on said base member surface.

16. A clamping head according to claim 15, wherein each of said first actuator ends is disposed adjacent to one of said respective first spring plate ends of each said spring plate of said first clamping unit,
   when said stopper plate rotates about said axis of rotation, said plurality of actuators also rotate about said axis of rotation, said second actuator end of each of said plurality of actuators take turn to enter into said recess to move away said stopper plate clamping surface to open said first space.

17. A clamping head according to claim 12, wherein each of said second actuator ends extends through one of said plurality of actuator apertures of said end plate.

18. A clamping head according to claim 12, wherein each of said first actuator ends extends through one of said plurality of actuator apertures of said end plate.

19. A clamping head according to claim 1, further comprising:
   a secondary clamping unit including at least two secondary spring plates arranged adjacent to each other on said plane traversing said axis of rotation of said stopper plate, each said secondary spring plate has a secondary first spring plate end comprising a secondary first spring plate clamping surface;
   a middle plate being arranged coaxially with said stopper plate and adjacent to said secondary clamping unit, said middle plate having a first middle plate surface opposing said stopper plate clamping surface and a second middle plate surface opposing said secondary first spring plate clamping surface of each said secondary spring plate;
   during rotation of said middle plate relative to said secondary clamping unit, said secondary clamping unit reciprocally moves away from and towards said middle plate such that a second space between said secondary first spring plate clamping surface of said second clamping unit and said second middle plate surface opens and closes for clamping hair.

20. A clamping head according to claim 19, wherein said two secondary spring plates intersect with each other orthogonally.

21. A clamping head according to claim 19, wherein each said secondary spring plate has a secondary second spring plate end opposing said secondary first spring plate end, said secondary first spring plate end has a first pair of wings on said secondary spring plate, and said secondary second spring plate end has a second pair of wings on said secondary spring plate, wherein said first pair of wings of said secondary spring plate are biased to a first direction from said secondary spring plate and said second pair of wings of said secondary spring plate are biased to a second direction from said secondary spring plate, wherein said first direction opposes said second direction.

22. An epilator comprising a clamping head and an actuating unit, wherein:
   the clamping head having a first clamping unit including at least two spring plates arranged adjacent to each other on a plane traversing an axis of rotation of a stopper plate, each said spring plate has a first spring plate end, comprising a first spring plate clamping surface, and a second spring plate end, opposing the first spring plate end and comprising a second spring plate clamping surface, wherein the first clamping unit does not engage with any coil spring, said stopper plate is adjacent to said first clamping unit and having a stopper plate clamping surface opposing said first spring plate clamping surface of each said spring plate, a first space is formed between said first spring plate clamping surface of each said spring plate and said stopper plate clamping surface for clamping hair;
   the actuating unit having a plurality of actuators being arranged along said axis of rotation, each of said plurality of actuators has a first actuator end adjacent to each end of each said spring plate of said first clamping unit; and
   when said stopper plate rotates about said axis of rotation, each of said plurality of actuators reciprocally moves away from and towards said stopper plate to open and close respective said first space.

* * * * *